(12) United States Patent
Kim et al.

(10) Patent No.: US 9,945,577 B2
(45) Date of Patent: Apr. 17, 2018

(54) AIR CONDITIONER HAVING A LIGHTING APPARATUS

(71) Applicant: LG ELECTRONICS INC., Seoul (KR)

(72) Inventors: Seulki Kim, Changwon-si (KR); Jihoon Choi, Changwon-si (KR); Yongseok Oh, Changwon-si (KR)

(73) Assignee: LG ELECTRONICS INC., Seoul (KR)

( * ) Notice: Subject to any disclaimer, the term of this patent is extended or adjusted under 35 U.S.C. 154(b) by 696 days.

(21) Appl. No.: 14/553,778

(22) Filed: Nov. 25, 2014

(65) Prior Publication Data

US 2015/0153062 A1    Jun. 4, 2015

(30) Foreign Application Priority Data

Nov. 25, 2013 (KR) .................. 10-2013-0144032

(51) Int. Cl.
*F24F 11/00* (2006.01)
*F25D 27/00* (2006.01)
(Continued)

(52) U.S. Cl.
CPC ......... *F24F 11/0086* (2013.01); *A61M 21/00* (2013.01); *A61M 21/02* (2013.01); *A61N 5/0618* (2013.01); *F24F 13/078* (2013.01); *F25D 27/005* (2013.01); *G05B 15/02* (2013.01); *H05B 33/0842* (2013.01); *H05B 37/0227* (2013.01); *H05B 37/0272* (2013.01);
(Continued)

(58) Field of Classification Search
CPC ............. F24F 13/078; F24F 2011/0058; F24F 2011/0091; F24F 2011/26; F24F 2221/02; F24F 11/0086
See application file for complete search history.

(56) References Cited

U.S. PATENT DOCUMENTS

| 2005/0109048 A1* | 5/2005 | Lee ........................ F24F 1/0007 62/126 |
| 2006/0021359 A1* | 2/2006 | Hur ........................ F24F 1/0007 62/126 |

(Continued)

FOREIGN PATENT DOCUMENTS

| CN | 1740003 | 3/2006 |
| CN | 101405507 | 4/2009 |

(Continued)

OTHER PUBLICATIONS

European Search Report issued in Application No. 14194758.0 dated May 15, 2015.
(Continued)

*Primary Examiner* — Jonathan Bradford
(74) *Attorney, Agent, or Firm* — KED & Associates, LLP

(57) ABSTRACT

An air conditioner is provided that may include a setting unit to set a predetermined function to be embodied or displayed with lighting, a storing unit to store at least one illumination pattern information, a control unit to connect the function input by the setting unit to an illumination pattern stored in the storing unit, and a lighting unit to be lighted according to the illumination pattern information connected to the function by the control unit.

46 Claims, 23 Drawing Sheets

(51) Int. Cl.
*A61N 5/06* (2006.01)
*G05B 15/02* (2006.01)
*H05B 37/02* (2006.01)
*H05B 33/08* (2006.01)
*A61M 21/02* (2006.01)
*F24F 13/078* (2006.01)
*A61M 21/00* (2006.01)

(52) U.S. Cl.
CPC ........... *A61M 2021/0044* (2013.01); *A61M 2205/3553* (2013.01); *A61M 2205/3569* (2013.01); *A61M 2205/3584* (2013.01); *A61M 2205/3592* (2013.01); *A61M 2205/505* (2013.01); *A61N 2005/0626* (2013.01); *A61N 2005/0636* (2013.01); *A61N 2005/0663* (2013.01); *F24F 2011/0058* (2013.01); *F24F 2011/0068* (2013.01); *F24F 2011/0091* (2013.01); *F24F 2221/26* (2013.01)

(56) References Cited

U.S. PATENT DOCUMENTS

2010/0084996 A1* 4/2010 Van De Sluis .... H05B 33/0863
315/312

2010/0175405 A1* 7/2010 Lee ...................... A61M 21/00
62/264

FOREIGN PATENT DOCUMENTS

| | | |
|---|---|---|
| CN | 101918094 | 12/2010 |
| CN | 102056373 | 5/2011 |
| CN | 102099630 | 6/2011 |
| CN | 102265096 | 11/2011 |
| CN | 102461338 | 5/2012 |
| CN | 202675472 | 1/2013 |
| CN | 102948261 | 2/2013 |
| CN | 202788030 | 3/2013 |
| EP | 1 806 159 | 7/2007 |
| EP | 2 206 986 | 7/2010 |
| EP | 2 306 103 | 4/2011 |
| EP | 2 607 799 | 6/2013 |
| WO | WO 2009/137904 | 11/2009 |

OTHER PUBLICATIONS

Chinese Office Action dated Feb. 4, 2017 issued in Application No. 201410687450.2 (with English Translation).

* cited by examiner (A)          (B)          (C)

(A)          (B)          (C)

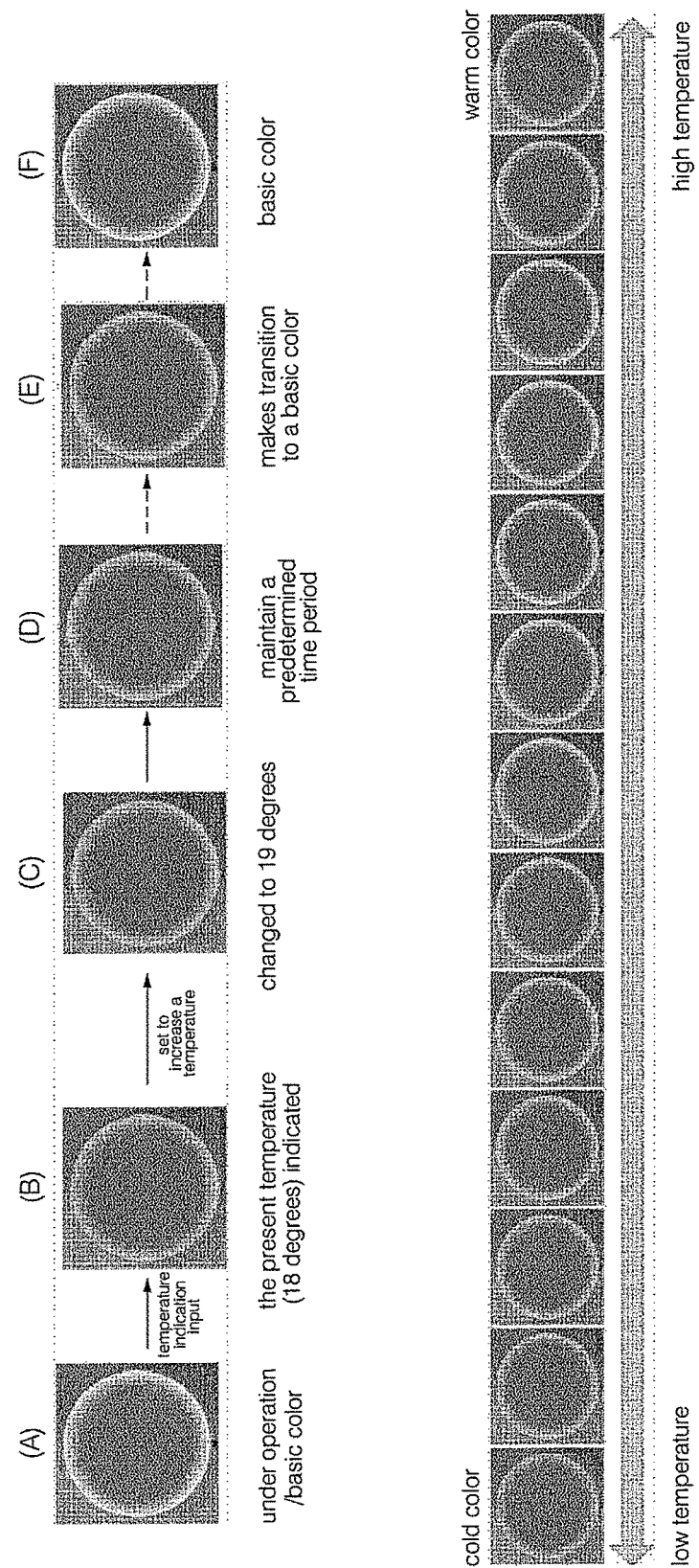

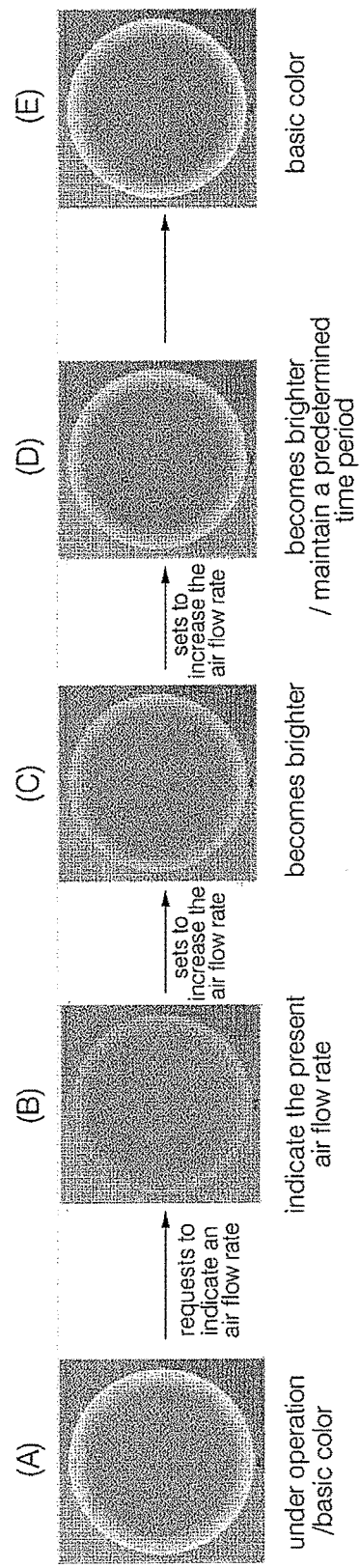

FIG. 12C
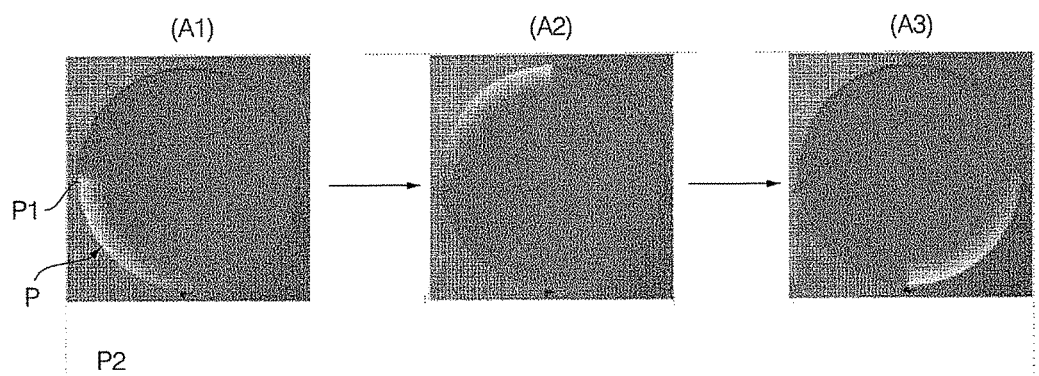
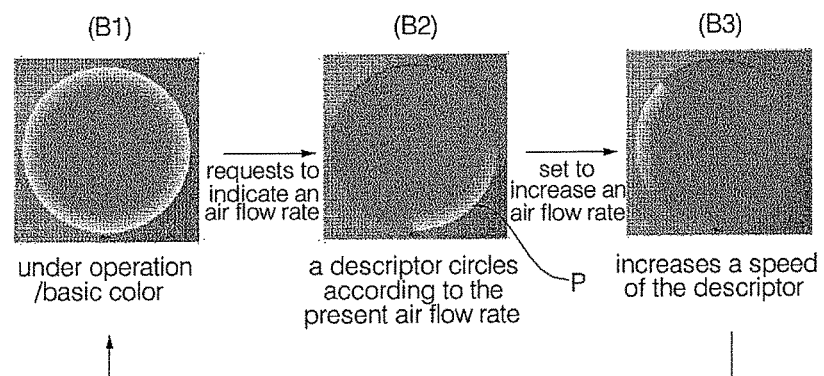
FIG. 12D
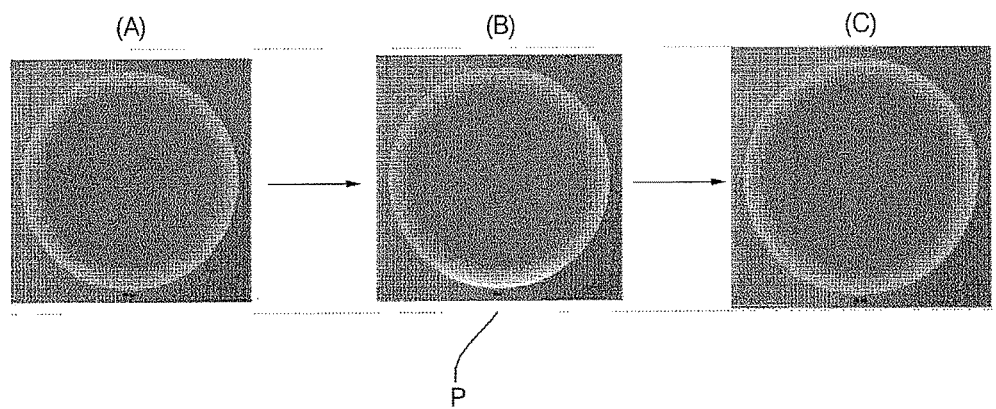

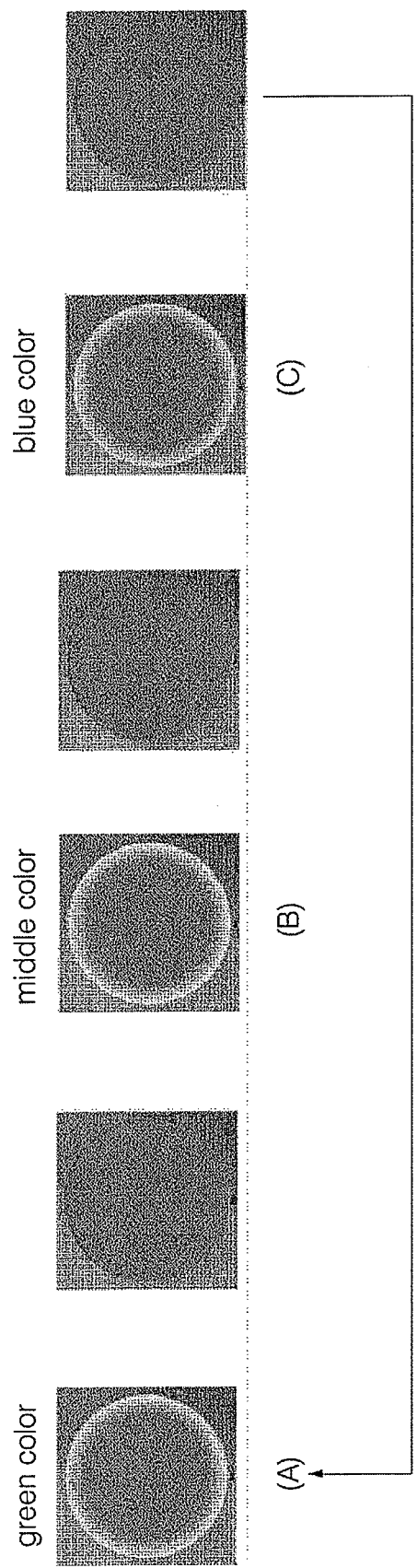

FIG. 17
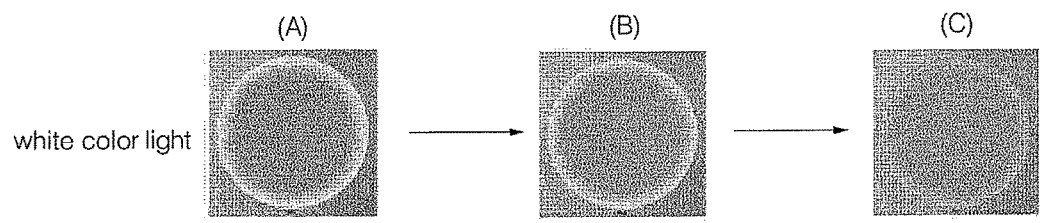
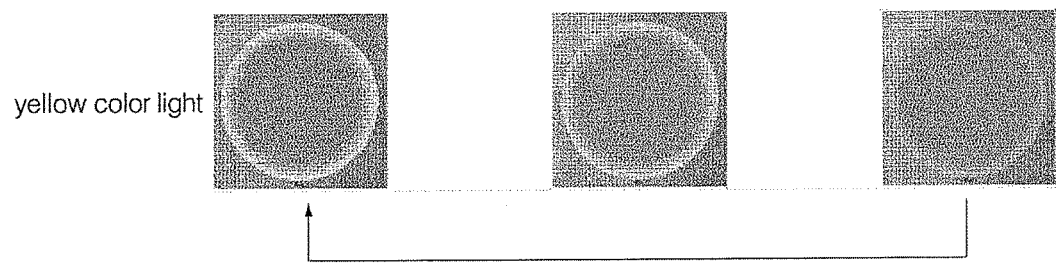
FIG. 18
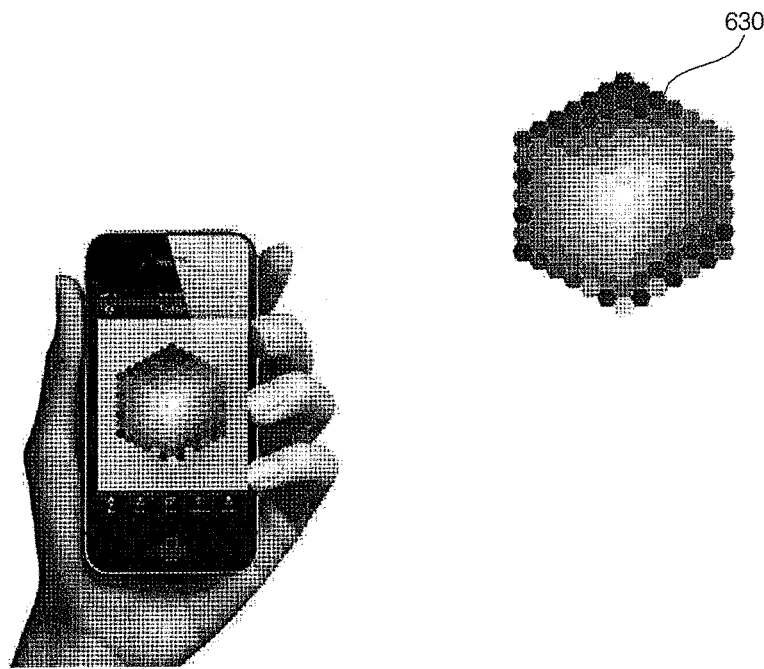

(A)　　　(B)　　　(C)　　　(D)　　　(E)

AIR CONDITIONER HAVING A LIGHTING APPARATUS

CROSS-REFERENCE TO RELATED APPLICATION(S)

This application claims priority under 35 U.S.C. § 119 to Korean Patent Application No. 10-2013-0144032 filed in Korea on Nov. 25, 2013, whose entire disclosure is hereby incorporated by reference.

BACKGROUND

1. Field

An air conditioner having a lighting apparatus is disclosed herein.

2. Background

An air conditioner is a machine for conditioning room air. In general, the air conditioner may be provided with an indoor unit or device and an outdoor unit or device connected by a refrigerant pipe line, to condition air by providing heat exchange between environment air and refrigerant as the refrigerant is passed through a phase change process of compression, condensation, expansion and evaporation while the refrigerant circulates in the refrigerant pipeline. The indoor unit may be installed in a room to discharge cooled or heated air to control a temperature of the room. However, in general, as changing a position of the indoor unit is difficult, once installed, the indoor unit is used fixed thereto, merely occupying a space when the indoor unit is not in use. Therefore, it is required to expand a purpose of use of the air conditioner by adding a function to the air conditioner besides the air conditioning function.

In general, an indoor unit body is provided with operation means or operator to operate the same or a display means or display to display an operation state. It is a recent trend in which exposure of the operation means or the display means is minimized to improve a sense of beauty. More particularly, in a case of the display means, even though the display means is an LCD, or LED panel, the display means has, not only inconvenience in that a user is required to come closer to the indoor unit for the user to have a good grasp of details displayed thereon, as the display means displays information using letters, but also a limitation in expanding a range of utilization of the display means to other functions because the function of the display means is limited to display of the information only.

Moreover, even if air conditioners having a function of lighting have been developed, the lighting provided on the air conditioners has a function of notifying a user of the air conditioner under operation only, and other ways of utilization of the air conditioner have not been adequate.

BRIEF DESCRIPTION OF THE DRAWINGS

Embodiments will be described in detail with reference to the following drawings in which like reference numerals refer to like elements, and wherein:

FIGS. 12A(A)~12A(F) illustrate a feed back light pattern when a temperature is changed as an example of information description lighting;

FIGS. 12B(A)~12B(E) illustrate an embodiment of a feed back light pattern when a flow rate is changed as an example of information description lighting;

FIGS. 12C(A1)~12C(B3) illustrate another embodiment of a feed back light pattern when a flow rate is changed as an example of information description lighting;

FIGS. 12D(A)~12D(C) illustrate an embodiment of a feed back light pattern as an example of information description lighting;

FIGS. 16B(A)~16B(C) illustrate a relaxation lighting as an example of therapy lighting;

FIGS. 17(A)~17(C) illustrate a mood lighting using a white light, and mood lighting using a yellow light, wherein the mood lightings have the same patterns with only a difference in color;

FIG. 18 illustrates a perspective view of designation of a light color on a mobile terminal;

DETAILED DESCRIPTION

Advantages, features and methods for achieving those will become apparent upon referring to embodiments described herein in detail together with attached drawings. However, embodiments are not limited to the embodiments disclosed hereinafter, but may be embodied in different modes. The embodiments are provided for perfection of disclosure and informing a scope to persons skilled in this field of art. Embodiments are defined only by scopes of claims. The same reference numbers will refer to the same elements throughout the specification.

Figure 1:
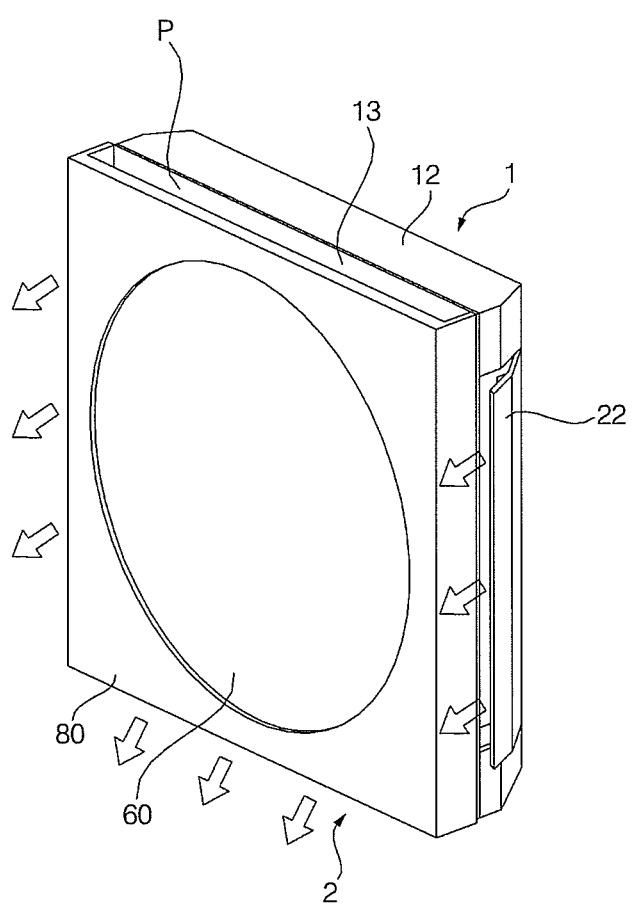
FIG. 1 is a perspective view of an air conditioner in accordance with an embodiment, in operation.
Figure 2:
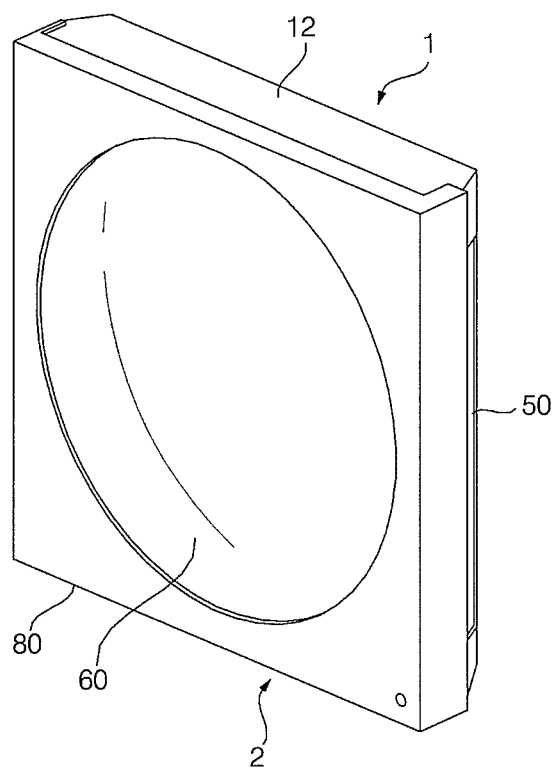
FIG. 2 is a perspective view of the air conditioner of FIG. 1, not in operation.
Figure 3:
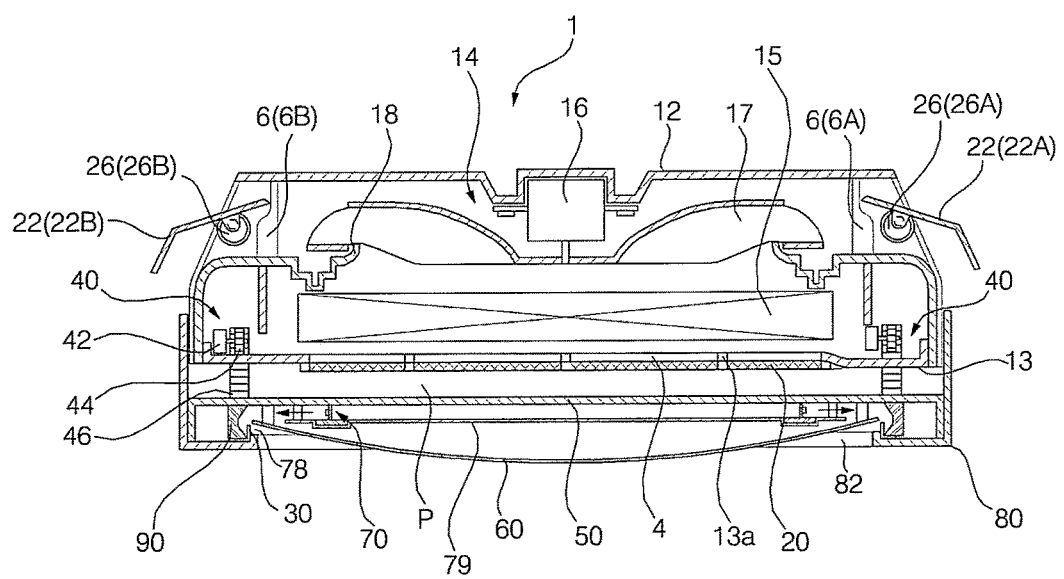
FIG. 3 is a lateral cross sectional view of the air conditioner of FIG. 1.
Figure 4:
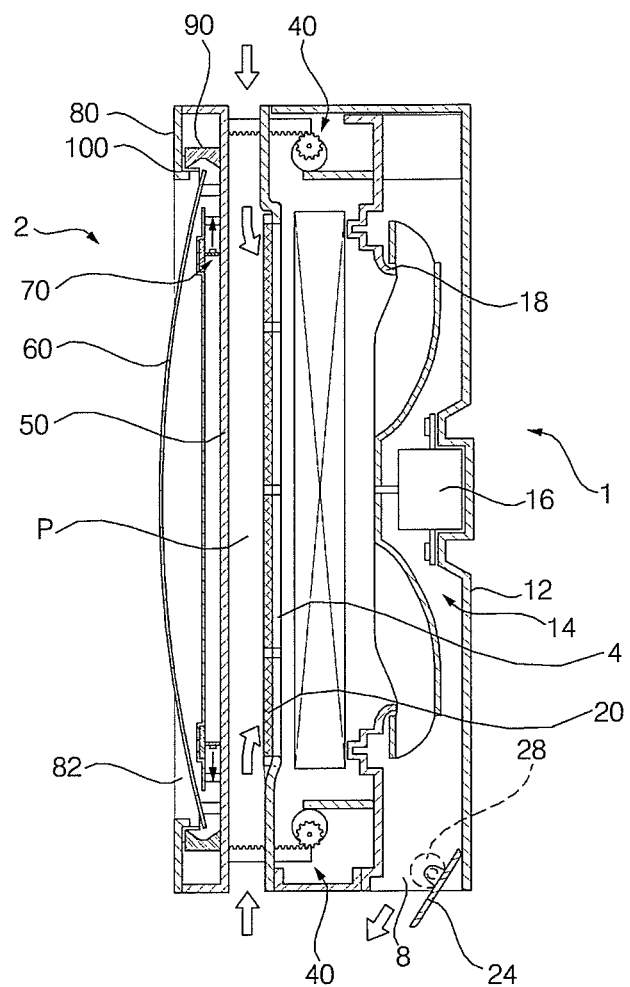
FIG. 4 is a longitudinal cross-sectional view of the air conditioner of FIG. 1, in operation.
Figure 5:
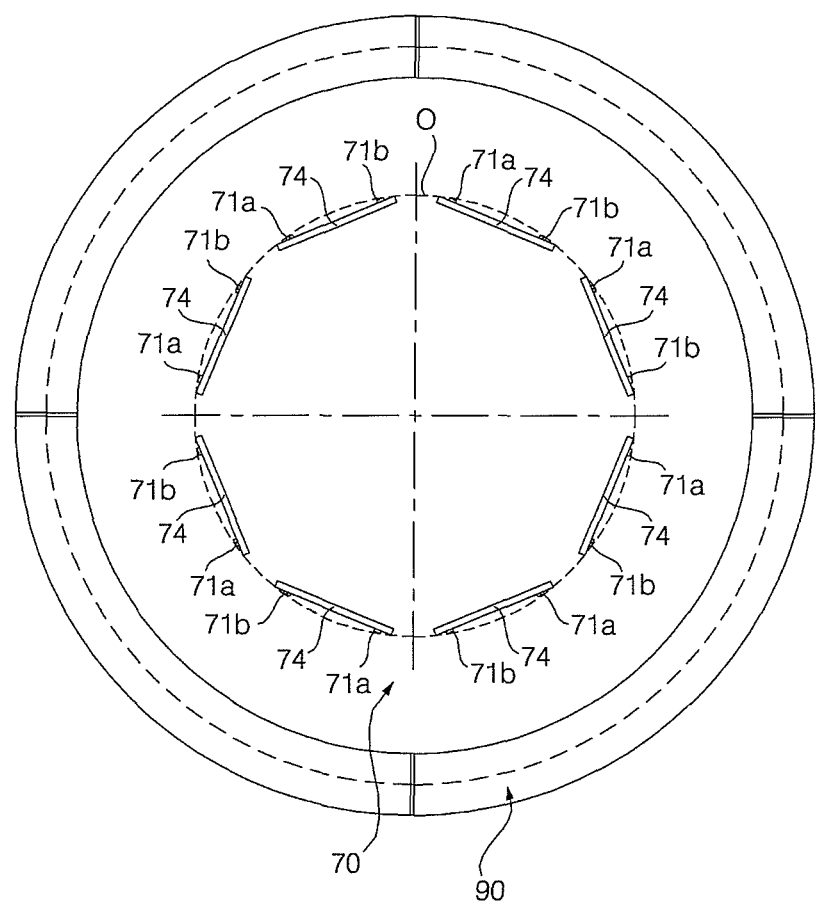
FIG. 5 is a front view of an inside of a lighting apparatus of the air conditioner of FIG. 1.
Figure 6:
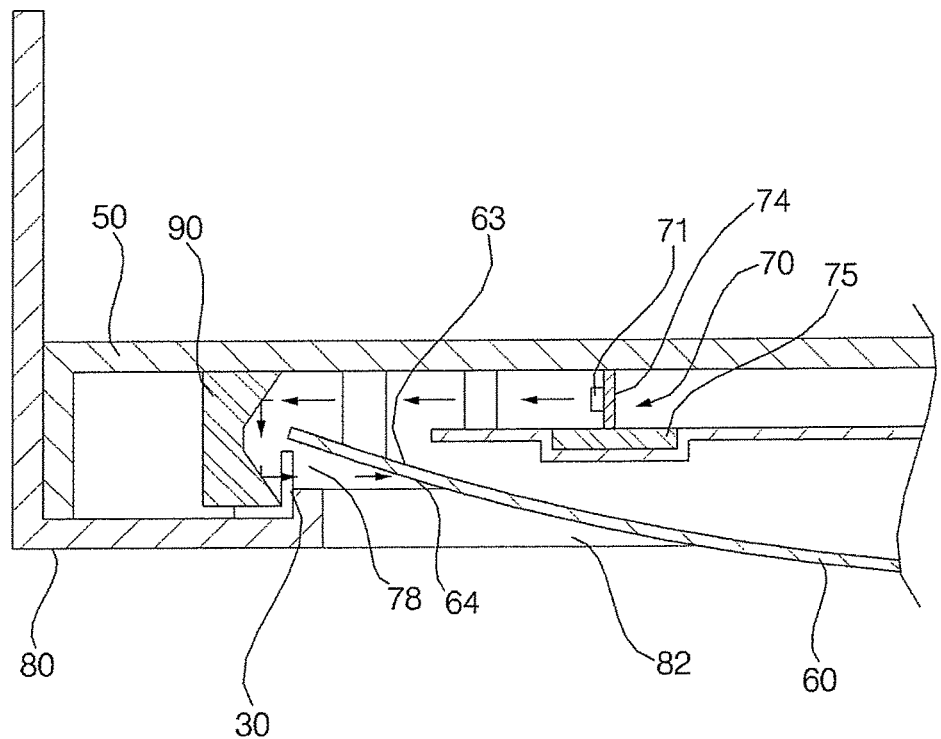
FIG. 6 is an enlarged sectional view of a portion of the lighting apparatus in the air conditioner of FIG. 1.

FIG. 1 is a perspective view of an air conditioner in accordance with an embodiment, in operation. FIG. 2 is a perspective view of the air conditioner of FIG. 1, not in operation. FIG. 3 is a lateral cross sectional view of the air conditioner of FIG. 1. FIG. 4 is a longitudinal cross sectional view of the air conditioner of FIG. 1, in operation. FIG. 5 is a front view of an inside of a lighting apparatus of the air conditioner of FIG. 1. FIG. 6 is an enlarged sectional view of a portion of the lighting apparatus in the air conditioner of FIG. 1.

Referring to FIGS. 1 to 6, the air conditioner according to embodiments may include a body 1, into which room air may be drawn, to heat exchange the room air with refrigerant and discharge the room air, and a lighting apparatus 2 mounted to the body 1. An air inlet 4, through which the room air may be drawn in, and at least one air outlet 6, 8 to discharge the air heat exchanged thus to a room may be formed in the body 1. A plurality of the air outlets may be formed to discharge the air to different directions.

The body 1 may include a rear case 12, and a front case 13 mounted in front of the rear case 12. The rear case 12 and the front case 13 may form an exterior appearance of the body 1. The front case 13 may have the air inlet 4 formed therein.

The lighting apparatus 2 may be provided to be movable in a forward and and backward direction. Hereinafter, movement of the lighting apparatus 2 in a direction closer to the body 1 may be referred to as "backward movement" and movement of the lighting apparatus 2 in a direction away from the body 1 may be referred to as "forward movement".

The air inlet 4 may be formed at a front of the body 1. The air inlet 4 may be opened in a frontward to rearward direction of the front case 13. The front case 13 may have a suction grill 13a provided thereto to filter foreign matter from the air being introduced into the air inlet 4.

The body 1 may have a plurality of air outlets 6 and 8 having discharge directions different from one another formed therein. The plurality of air outlets 6 and 8 may include at least one lateral direction air outlet 6 to discharge the air in a lateral direction of the body 1, and a lower direction air outlet 8 to discharge the air in a lower direction of the body 1. The lateral direction air outlet 6 may be provided at both sides of the body 1. Herein, the lateral direction air outlet that discharges air in a left of first direction of the body 1 may be referred to as a first direction air outlet 6A, and the lateral direction air outlet that discharges air in a right or second direction of the body 1 will be referred to as a second direction air outlet 6B.

The body 1 may have a fan unit or assembly 14 and a heat exchanger 15 mounted thereto. The fan unit 14 may be provided to blow air from the air inlet 4 to the air outlets 6 and 8, and the air may pass through the heat exchanger 15 and may heat exchange while passing through the heat exchanger 15. Depending on arrangements of the air inlet 4 and the air outlet 6 and 8, the fan unit 14 may include a centrifugal type fan which draws in air in an axial direction and discharges the air in a radial direction, or an axial type fan which draws in air in the axial direction and discharges the air in the axial direction. In a case of a centrifugal fan 14, the centrifugal fan unit 14 may include a motor 16 mounted to the rear case 12, and a centrifugal fan 17 rotated by the motor 16. The centrifugal fan unit 14 may further have an orifice 18 to guide the air to the centrifugal fan 17.

There may be a filter 20 to filter the air drawn into the air inlet 4. For conveniences of maintenance or replacement, the filter 20 may be detachably mounted to the front case 13. The filter 20 may be arranged at a fore end of the suction grill 13a.

At a moved forward position, the lighting apparatus 2 may form a passage, that is, an air flow passage P, between the lighting apparatus 2 and the body 1 for the air to move to the air inlet 4. The room air is drawn into the air inlet 4 along the air flow passage P.

The body 1 may include a lateral direction discharge vane 22 to control an air flow rate being discharged through the lateral direction air outlet 6, and a lower direction discharge vane 24 to control an air flow rate being discharged through the lower direction air outlet 8. The lateral direction discharge vane 22 may rotate around a vertical shaft, to open and close the lateral direction air outlet 6. By controlling rotation of the lateral direction discharge vane 22, a left/right or lateral wind direction of the air being discharged through the lateral direction air outlet 6 may be controlled. The lateral direction discharge vane 22 may include a left or first direction discharge vane 22A to open and close the left direction air outlet 6A, and a right or second direction discharge vane 22B to open and close the right direction discharge vane 6B. The lower direction discharge vane 24 may rotate around a horizontal shaft to control a vertical wind direction of the air being discharged through the lower direction air outlet 8.

The air conditioner may include a lateral direction discharge vane drive mechanism 26 to rotate the lateral direction discharge vane 22, and a lower direction discharge vane drive mechanism 28 to rotate the lower direction discharge vane 24. Each of the lateral direction discharge vane drive mechanism 26 and the lower direction discharge vane drive mechanism 28 may include a motor to provide a torque thereto. The lateral direction discharge vane drive mechanism 26 may include a left or first direction discharge vane drive mechanism 26A to rotate the left direction discharge vane 22A, and a right or second direction discharge vane drive mechanism 26B to rotate the right direction discharge vane 22B.

The lighting apparatus 2 may be arranged in front of the air inlet 4. As the air inlet 4 is shaded or covered by the lighting apparatus 2, an entire exterior appearance of the air conditioner may be beautiful. The lighting apparatus 2 may have a size formed larger than the air inlet 4. In this case, the air inlet 4 may be completely shaded or covered by the lighting apparatus 2. Thus, the lighting apparatus 2 may function as a decorative apparatus to enhance a decorative beauty of the air conditioner, or may function as a display that displays certain information with an illuminated image or a varying pattern of the illuminated image.

A lighting apparatus drive mechanism 40 may move the lighting apparatus 2 in the forward and backward direction. The lighting apparatus drive mechanism 40 may include a motor 42 to provide a torque, a driving gear rotated by the motor 42, and a driven gear engaged with the driving gear to move together with the lighting apparatus 2. The driving gear may include a pinion 44, and the driven gear may include a rack 46 engaged with the pinion 44.

To stably drive the lighting apparatus 2, a plurality of the lighting apparatus drive mechanisms 40 may be provided. According to one embodiment, the lighting apparatus drive mechanisms 40 may be provided on a left or first lateral side and a right or second lateral side of the lighting apparatus 2. When the air conditioner is operated, as the lighting apparatus 2 is moved forward by the lighting apparatus drive mechanism 40, the air flow passage P may be formed between the body 1 and the lighting apparatus 2.

The lighting apparatus 2 may include a lighting unit 70 to emit light, a base 50 to support the lighting unit 70, an illumination plate 60, a frame 80 having an opening 82 formed therein to expose at least a portion of the illumination plate 60 to an outside of the air conditioner and having a circumference thereof which forms a gap 78 to the illumination plate 60, and a reflective body 90 to reflect light emitted from the lighting unit 70 toward the gap 78. The base 50 and the frame 80 may be moved as one unit by the lighting apparatus drive mechanism 40.

The lighting unit 70 may include a plurality of light source elements 71. Depending on turning on/off patterns of the plurality of light source elements 71, an illuminated image formed on the illumination plate 60 may vary. The illuminated image may be formed on a predetermined path formed according to an array mode of the plurality of light source elements 71, and may move along the path according to the turning on/off pattern of the plurality of light source elements 71. Hereafter, though an example will be discussed, in which the plurality of light source elements 71 are arranged along a closed path (hereafter, referred to as annular path 0), and the illuminated image is also formed along a predetermined closed path matched thereto, embodiments are not limited thereto.

Though the plurality of light source elements 71 may be mounted on one circuit board, the plurality of light source elements 71 may also be mounted on a plurality of circuit boards 74. The plurality of circuit boards 74 may be mounted to an annular main circuit board 75, and the main circuit board 75 may be fixedly secured to the base 50 or the frame 80 with a supporter 79. The supporter 79 may shield the light emitted from the light source elements 71 incident on a rear side 63 of the illumination plate 60. By controlling lighting conditions, such as an order of turning on/off, colors, brightness, and so on of the plurality of the light source elements 71, a variety of illuminated images may be formed on the illumination plate 60.

The gap 78 may have a light transmission cover 30 arranged thereto for transmission of the light reflected by the reflective body 90. The light transmission cover 30 may be formed of a transparent, or semitransparent material that diffuses the light transmitted therethrough, providing a misty illumination.

The circuit board 74 may be arranged such that a side having the plurality of light source elements 71 mounted thereto faces the reflective body 90. Such a structure enables, not only to secure adequate light quantity incident on the reflective body 90, but also to shield the light incident on a side the rear side of the circuit board 74 faces, such that a center portion of the illumination plate 60 forms a dark portion which provides contrast with an outer portion of the illumination plate 60 adjacent to the gap 78, providing the misty illumination in which darkness is smoothly graded from the center portion to the outer portion of the illumination plate 60.

One circuit board 74 may have a plurality of the light source elements 71a and 71b mounted thereto. The plurality of the light source elements 71a and 71b may be turned on or turned off together, or turned on/off with time differences according to a predetermined turn on/off pattern. All of the light source elements 71 of the lighting unit 70 may embody different modes of animated illumination by a predetermined turn on/off pattern in which all of the light source elements 71 interact.

Though the illumination plate 60 may be formed of a non-transparent material, embodiments are not limited thereto. That is, the illumination plate 60 may be formed of a material having a predetermined transparency. However, even in this case, it is required that the light quantity transmitted from the rear side 63 to a front side 64 of the illumination plate 60 is lower than the light quantity incident on the front side 64 through the gap 78.

The illumination plate 60 may have a concave surface, for which a center portion of the front side 64 on which the light transmitted through the gap 78 is incident, protrudes forward compared to a peripheral portion, to increase an area of light incident, enabling to make a distinctive contrast of the darkness between the peripheral portion and the center portion, and providing a three dimensional effect.

Each of the plurality of light source elements 71 may have controllable color and brightness. As a method for embodying a lighting color of the plurality of light source elements 71, an RGB color model is known widely in which a red color light, a green color light, and a blue color light are added in a proper ratio, to embody or display a desired color. As the plurality of light source elements 71 which can express a color according to an input ratio of the red color light, the green color light, and the blue color light, there may be LED, LCD, for example. The plurality of light source elements 71 may express or display a color according to input of an array of R, G, B in which the ratio of the red color light, the green color light, and the blue color light is indicated with numerical values between 0 to 255. Each of the light source elements 71 may vary in brightness thereof with current intensity.

The color of the lighting may be defined with a visible light spectrum, relatively. A plurality of RGB color tables are known, in which colors are divided by using the RGB array. Each of the colors indicated on these color tables may be matched to a color classification with reference to the spectrum. For example, if a red color is defined to have a wave length of about 660 nm, a green color is defined to have a wave length of about 532 nm, and a blue color is defined to have a wave length of about 450 nm, the red color, the green color, and the blue color defined by the RGB array may be defined as ones most close to the same colors on the spectrum within a wave length range which may be embodied by the plurality of light source elements 71. The colors classified according to the RGB array may be divided according to relative positions of wave lengths on the spectrum of the visible light matched to the colors. For example, an orange color light falls under a region between the red color light and the yellow color light, and indicated with the RGB array matched to the regions. Moreover, if it is assumed that lighting of a blue color group or a red color group may be selected using the lighting apparatus 2, a color of the lighting emitted when the blue color group is selected is a predetermined color closer to the blue color on the visible light spectrum than when lighting of the red color group is selected, and, in an opposite case, a predetermined color closer to the red color.

The plurality of the light source elements 71 may be arranged along a circle 0 substantially, such that each of the plurality of light source elements 71 emits the light to an outside in a radial direction, that is, radially, from a center of the circle 0. The plurality of circuit boards 74 may be mounted to the main circuit board 75 spaced therefrom. The plurality of circuit boards 74 may be mounted to the main circuit board 75 to face directions different from one another. The plurality of circuit boards 74 may be mounted such that sides thereof are opposite to an inside periphery of the reflective body 70. The light source elements 71a, 71b may be mounted on one of two sides of the circuit board 74 opposite to the reflective body 90, and the light source elements 71 may direct the light toward the inside periphery of the reflective body 90. All of the plurality of the light source elements 71 may be turned on at a same time, or when some of the light source elements 71 are turned on, the rest of the plurality of light source elements 71 may be turned off.

Hereafter, an image illuminated on the illumination plate 60 at a time point will be referred to as a 'descriptor', and a pattern of movement, formation, disappearance, shape change, color, and illuminance change of the descriptor may be referred to as an 'illumination pattern'.

Figure 7:
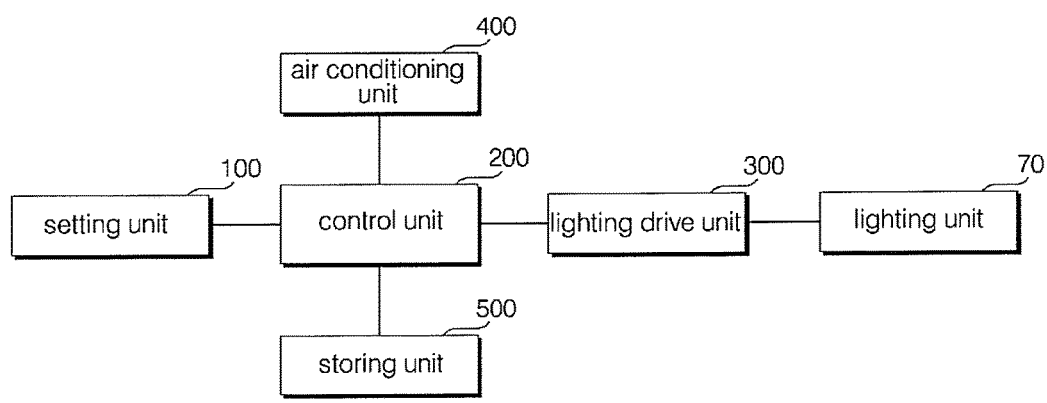
FIG. 7 is a block diagram of control elements of the air conditioner of FIG. 1.

FIG. 7 is a block diagram of control elements of the air conditioner of FIG. 1. Referring to FIG. 7, the air conditioner may include a setting unit or device 100, a control unit or controller 200, a lighting drive unit or device 300, a lighting unit 70, a storing unit or storage 500, and an air conditioning unit or device 400.

The setting unit 100 may set a function to be embodied or displayed with lighting. The function to be embodied or displayed with lighting may be active lighting, information description lighting, therapy lighting, mood lighting, or obzee (image) description lighting, for example. The setting unit 100 may include an input to receive input on selection of the active lighting, information description lighting, therapy lighting, mood lighting, or obzee description lighting.

The active lighting may set an illumination pattern according to a surrounding environment at a time of turning on, wherein the surrounding environment may be a meteorological condition of a region, such as a room temperature, season and time, weather, sun rise/sun set, and/or an outdoor temperature, for example. For example, the active lighting may be applied to wake-up lighting, or sleep lighting. The air conditioner may include an input unit or input (not shown) to receive input on a setting of a scheduled time or a time of the wake-up lighting (or, sleep lighting), and the control unit 200 may control the lighting unit 70 to be turned on according to the scheduled wake-up lighting setting received through the input unit. In this case, the lighting described with the lighting unit 70 may have a pattern thereof fixed according to the surrounding environment of an embodying time point of the pattern (for example, a turning on time point of the lighting unit 70 due to arrival of the scheduled time). The wake-up lighting may provide an illumination pattern (hereinafter, a "wake-up illumination pattern") which may remind a user of morning sun shine, and the sleep lighting may provide an illumination pattern (hereinafter, a "sleep illumination pattern") which may remind a user of moon light at dawn. The illumination patterns will be described in detail hereinbelow.

The information description lighting may be description of operation information, such as an operation state, and feed back on operation, instruction, order to the air conditioner, displayed with the lighting for a user to recognize, enabling the user to recognize the operation state of the air conditioner only with the lighting without an LCD or LED panel, or an output from a speaker, used in the related art. The information description lighting may include description of power on for putting the air conditioner into operation, power off for stopping operation of the air conditioner, putting a cooling/heating operation mode into operation, or shifting modes between the cooling/heating operation modes, changing a set temperature, changing an air flow rate, for describing a response (or, feed back) to reception of a predetermined control order at a time the control order is received from a remote control means, such as a remote controller, for example. Though not shown, the air conditioning unit may further include a reception unit or device that receives the control order, and the control unit 200 may control the lighting unit 70 and/or the air conditioning unit 400 according to the control order received through the reception unit. The pattern of the information description lighting (hereinafter, an "information description illumination pattern") will be described in detail hereinbelow.

The therapy lighting is utilization of study results that lighting influences the human body when colors of the lighting are varied. With many studies, it has been verified that the lighting influences the human body when lighting colors (or, wave lengths of the lighting) are varied, not only in view of sensibility, but also in view of mind, and biology. The illumination pattern for embodying the therapy lighting (hereafter, a "therapy illumination pattern") will be described in more detail hereinbelow.

In general, a room space in which an air conditioner is operated has a room light provided on a ceiling. As a function of the room light is aimed at lighting the room, it is difficult to change the lighting pattern of the lighting. The mood lighting in this embodiment functions as a supplementary lighting to change a room environment (mood) by changing a predetermined mood illumination pattern with the lighting unit 70.

The patterns (hereafter, a "mood illumination pattern") for embodying or displaying the mood lighting will be described in more detail hereinbelow.

The obzee description lighting describes an obzee which reminds a user of an object of description, such as a predetermined work of art, and a natural object with the lighting apparatus 2. The lighting apparatus 2 may be utilized as a room decoration. The illumination pattern (hereafter, an "obzee description illumination pattern") for embodying or displaying the obzee description lighting will be described in more detail hereinbelow.

The storing unit 500 is a writing medium for storing information on the illumination patterns to be embodied with the lighting unit 70 (hereafter, "illumination pattern information") and different pieces of information including an algorithm for controlling the lighting unit 70. The control unit 200 may perform general operation control of the air conditioner based on the information written on the storing unit 500.

The storing unit 500 may be a volatile or non-volatile recording medium, and, depending on embodiments, may include, but is not limited to, EEPROM (Electronically Erasable ad Programmable Read Only Memory). The EEPROM can maintain information written thereon without erasure even if power supply is cut-off following turn off of the power.

The air conditioning unit 400 may discharge conditioned air into the room, and include components involved in air conditioning. The components may include the body 1, the motor 16, and the driving mechanisms 26, 28, and 40.

The control unit 200 may control general operation of the air conditioner. Along with control of an air conditioning function of the body 1, the control unit 200 may generate a predetermined control signal according to an illumination pattern matched to a function selected at the setting unit 100 from illumination patterns stored in the storing unit 500, and apply the control signal to the lighting drive unit 300. By driving the lighting unit 70 according to the control signal, the lighting drive unit 300 may display the illumination pattern matched to the function selected at the setting unit 100.

Figure 8:
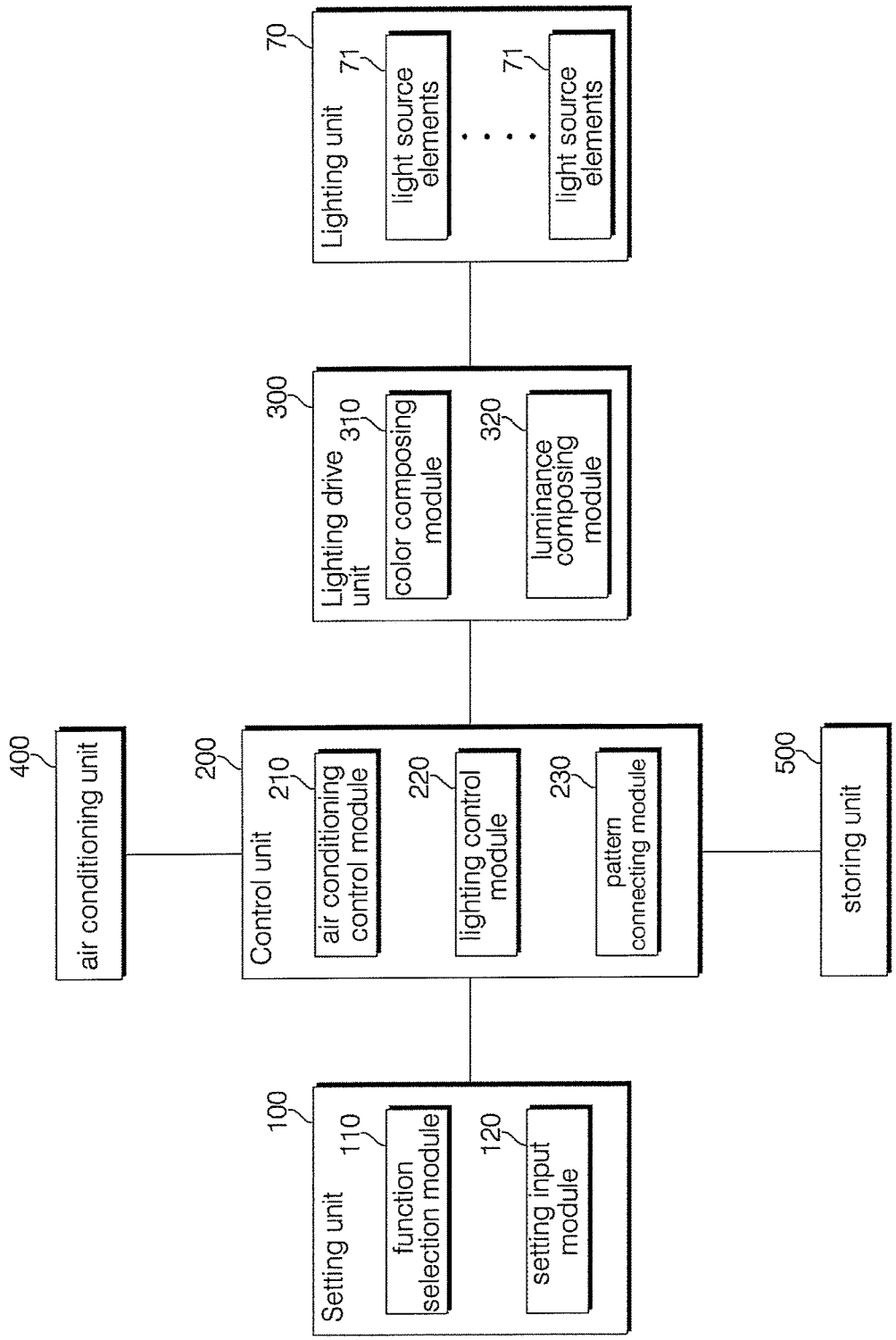
FIG. 8 is a block diagram of control elements of an air conditioner in accordance with another embodiment.

FIG. 8 is a block diagram of control elements of an air conditioner in accordance with another embodiment. Referring to FIG. 8, setting unit 100 may include a function selection module 110 for selection of a function to be embodied with the lighting, and a setting input module 120 to receive a setting on the function selected at the function selection module 110. The active lighting, the information description lighting, the therapy lighting, the mood lighting or the obzee description lighting may be selected using the function selection module 110.

Depending on embodiments, the function selection module 110 may include a function selection means or selector (not shown) to receive selection of a function to be embodied or displayed with the lighting from the user, directly. In this case, the setting input module 120 may include a setting input (not shown) to receive a setting on the function selected at the input from the user, directly. Different from this, the function selection module 110 may select a preset or predetermined function automatically according to a predetermined algorithm in the middle of an operation of the air conditioner, which is most suitable for embodying or displaying the information description lighting.

In the meantime, the setting input module 120 may communicate with an external information providing apparatus (not shown) through a wire or wireless communication network, and may include a communication module (not shown) to receive a setting on a selected function. In this case, the setting on the function selected at the function selection module 110 may be provided from the information providing apparatus. As the communication network, a Wi-Fi communication network may be utilized, which may access a domestic AP (Access Point). The Wi-Fi is a WLAN (Wireless Local Area Network) which meets an IEEE (Institute of Electronics Engineer) 802.11 standard.

Control unit 200 may include an air conditioning control module 210 to control the air conditioning unit 400, a pattern connecting module 230 to connect or match an illumination pattern to a function selected at the function selection module 110 from the illumination patterns stored in the storing unit 500, and a lighting control module 220 to generate a control signal according to the illumination pattern connected or matched by the pattern connecting module 230 to the selected function, and apply the control signal to the lighting drive unit 300.

The control signal generated by the lighting control module 220 may include information on a color and brightness. The lighting drive unit 300 may include a color composing module 310 to generate R, G, B set values according to the RGB array from the control signal to be forwarded to the plurality of light source elements 71 to be turned on according to the illumination pattern, and a luminance composing module 320 to generate a luminance of the plurality of light source elements 71 according to luminance information of the control signal. The luminance of the plurality of light source elements 71 may vary with intensity of a current applied thereto. The color and luminance of the descriptor embodied or displayed with the lighting may be controlled by the color composing module 310 and the luminance composing module 320.

Figure 9:
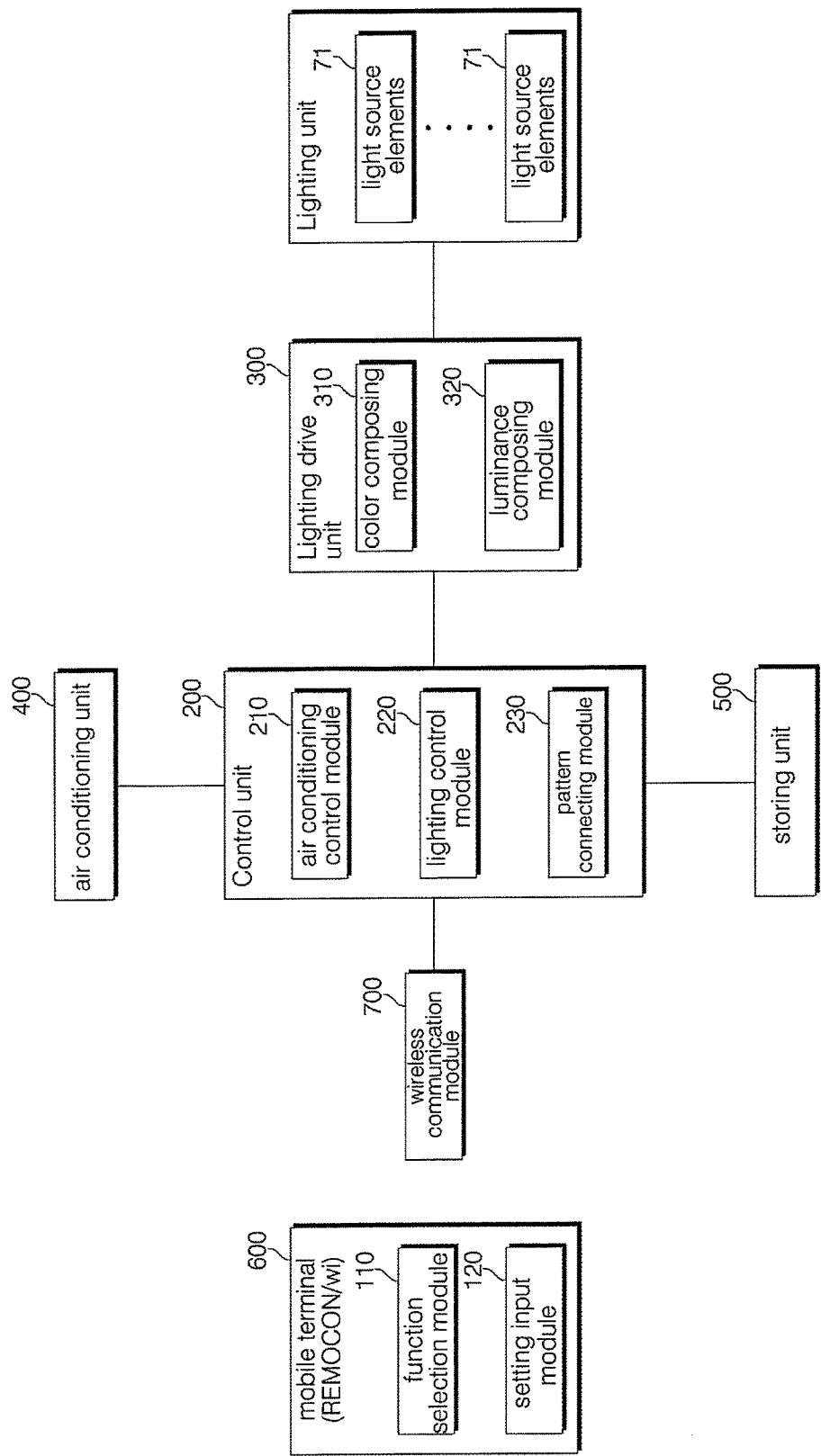
FIG. 9 is a block diagram of control elements of an air conditioner in accordance with another embodiment.

FIG. 9 is a block diagram of control elements of an air conditioner in accordance with another embodiment. Referring to FIG. 9, the air conditioner may include a wireless communication module 700 provided in body 1 or lighting apparatus 2, and a mobile terminal 600 for wireless communication with the wireless communication module 700. The mobile terminal 600 may be a remote controller provided together with the air conditioner, or a smart phone that communicates with the air conditioner through a Wi-Fi communication network. Hereafter, an air conditioning system is defined as an entire system including an air conditioner and a smart phone.

Function selection module 110 and/or setting input module 120 may be provided in the mobile terminal 600. The wireless communication module 700 may be provided in the body 1 or the lighting apparatus 2 of the air conditioner for communication with the mobile terminal 600 to receive information from the function selection module 110 or the setting input module 120. This embodiment is identical to the previous embodiment in view of relations among units or modules except that the function selection module 110 or the setting input module 120 is provided in the mobile terminal 600 and the wireless communication module 700 is provided in the body 1 or the lighting apparatus 2.

Figure 10:
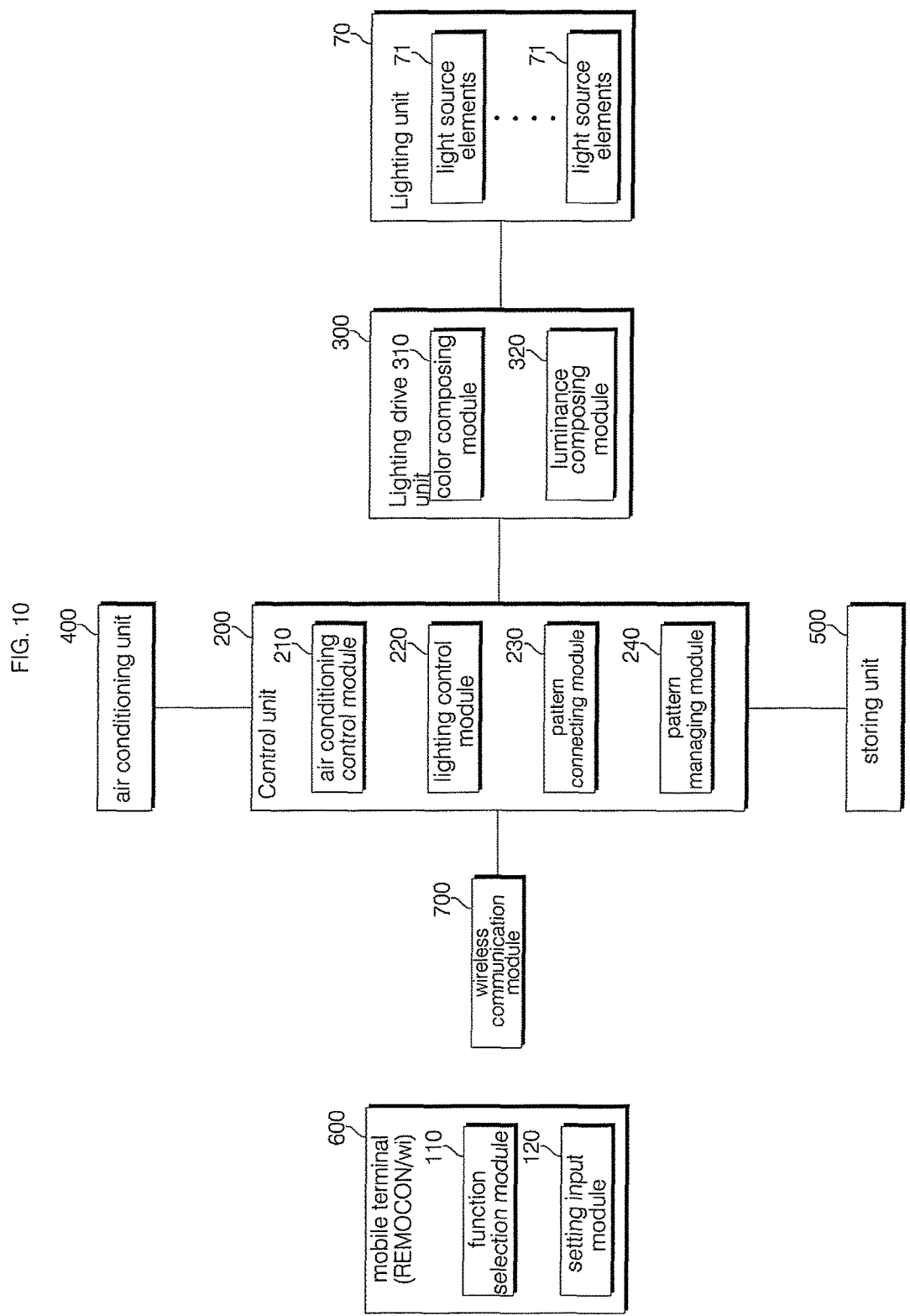
FIG. 10 is a block diagram of control elements of an air conditioner in accordance with another embodiment.

FIG. 10 is a block diagram of control elements of an air conditioner in accordance with another embodiment. Referring to FIG. 10, mobile terminal 600 may access an information providing apparatus far away therefrom with an AP (Access Point) connected to a network, such as the Internet, may download update information on functions and/or functions of illumination patterns intended to be described or displayed by the lighting, and may store the update information in the storing unit 500 by communication with the wireless communication module 700.

Control unit 200 may include a pattern management module 240 to manage the illumination patterns stored in the storing unit 500 based on update information received through the wireless communication module 700. The pattern management module 240 may update the storing unit 500 by adding, erasing, and changing the illumination patterns therein, for example.

Figure 11A:
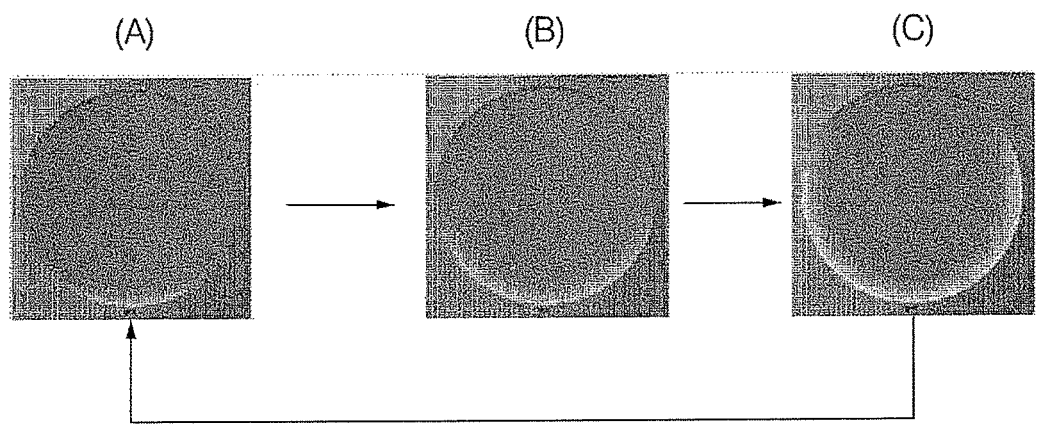
FIGS. 11A(A)~11A(C) illustrate a wake up light pattern as an example of an active lighting, and FIGS. 11B(A)~11B(C) illustrates a sleep light pattern as an example of the active lighting.
Figure 11B:
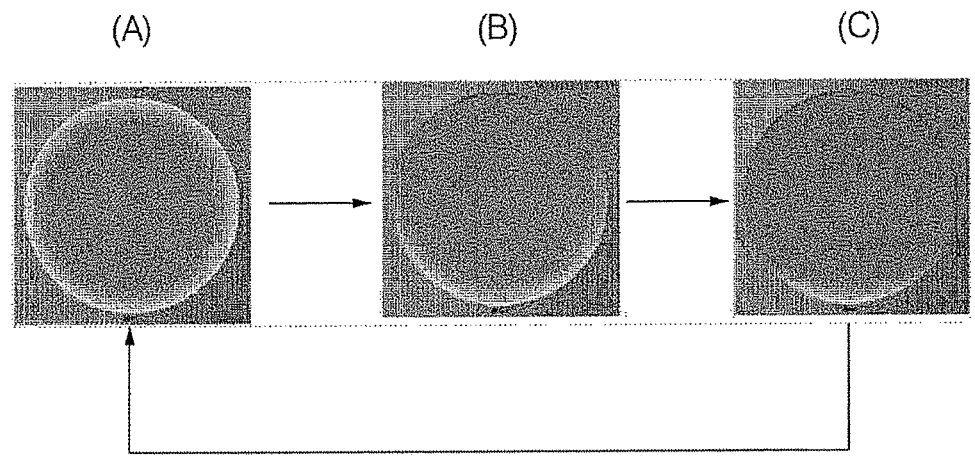

FIGS. 11A(A)~11A(C) illustrate a wake up light pattern as an example of an active lighting, FIGS. 11B(A)~11B(C) illustrate a sleep light pattern as an example of the active lighting. The active lighting may be selected with the function selection module 110. FIGS. 11A(A)~11A(C) illustrate an illumination pattern in a case in which the wake-up lighting is selected as an example of the active lighting with the function selection module 110.

In the state in which the wake-up lighting is selected, a setting for the wake-up lighting selected thus may be input with the setting input module 120. As the setting for the wake-up lighting, there may be a scheduled turn on time, and a weather condition of the region at the scheduled turn on time. If the wireless communication module 700 is provided, the weather condition at the scheduled turn on time may be set in real time with wireless communication.

The pattern connecting module 230 may connect or match one of the illumination patterns stored in the storing unit 500 to the setting set with the setting input module 120. The storing unit 500 may store a plurality of pieces of illumination pattern information classified according to functions to be embodied or displayed with the lighting unit 70. Of the plurality of pieces of illumination pattern information, the pattern connecting module 230 may connect or match the illumination pattern information to the function set with the setting unit 100.

Upon arrival of the scheduled turn on time (a scheduled condition is met), the lighting control module 220 may generate a control signal according to the illumination pattern connected thus and apply the control signal to the lighting drive unit 300. If the weather of the region is reflected in real time, the connection to the wake-up illumination pattern, and the composition of the control signal according to the wake-up illumination pattern connected thus may be made according to a weather state at the time of arrival of the scheduled turn on time, or according to the weather state updated at a most recent time from the scheduled turn on time.

As the wake-up illumination pattern is for reminding the user of morning sunshine to induce a natural wake-up, it is suitable that the wake-up illumination pattern is a pattern of a warm color group, such as yellow, orange, and red. The color composing module 310 may drive the plurality of light source elements 71 to provide a light in the warm color group.

The wake-up illumination pattern may be displayed by turning on some of the light source elements 71 (see FIG. 11A(A)), and thereafter, the light source elements 71 around the light source elements 71 turned on thus may be turned on (see FIGS. 11A(B) and 11A(C)). Such an illumination pattern may be embodied by controlling turning on of the light source elements 71 with the luminance composing module 320. The lighting according to the wake-up illumination pattern may be performed repeatedly until there is a user's response (cancellation of the scheduled turn on time), or for a preset or predetermined time period.

Referring to FIGS. 11B(A)-11B(C), the sleep illumination pattern is for reminding the user of moon light to induce a comfortable sleep, and may be utilized when a scheduled condition, such as scheduled sleep or scheduled turn off is met. As the sleep illumination pattern, a pattern of a cold color group, such as blue or violet, is suitable. The color composing module 310 may drive the plurality of light source elements 71 to provide a light in the cold color group.

The sleep illumination pattern may be displayed by turning off some, or all of the light source elements 71 (see FIG. 11B(A)), and thereafter, the light source elements 71 around the light source elements 71 turned off thus may be turned off (see FIG. 11B(B)) until a preset or predetermined number of light source elements are left on (see FIG. 11A(C)). Such an illumination pattern may be embodied by controlling turning off of the light source elements 71 with the luminance composing module 320. The lighting according to the sleep illumination pattern may be performed repeatedly until there is a user's response (cancellation of the scheduled turn off time), or for a preset or predetermined time period.

FIGS. 12A(A)~12A(F) illustrate a feed back light pattern when a temperature is changed as an example of information description lighting. The air conditioner may include an input to receive a user's setting on a desired room temperature, for the air conditioning control module 210 to control the air conditioning unit 400 according to the set room temperature to make the room temperature reach the set temperature. If the set temperature is changed through the input, the control unit 200 may compose or display a feed back illumination pattern according to the temperature change. The feed back illumination pattern may be provided to notify the user of a regular input of the temperature change request through the input, and has an effect of performing a notifying function only with lighting without a separate display.

In more detail, of the illumination patterns in the storing unit 500, the pattern connecting module 230 may connect or match the feed back illumination pattern (hereafter, "temperature changing feed back illumination pattern") to a set temperature change, and the lighting control module 220 may generate a control signal according to the temperature changing feed back illumination pattern connected thus and apply the control signal to the lighting drive unit 300.

The temperature changing feed back illumination pattern may indicate an increase or decrease of the set temperature with a pattern of lighting of which a color varies. The color of the lighting may be classified into a warm color group, which gives a warm feeling to a user, and a cold color group, which gives a cold feeling. The temperature changing feed back illumination pattern may be a pattern of which a color temperature of the lighting makes a transition toward a high temperature if a set temperature to be changed is higher than the present set temperature (increase of the set temperature), and opposite to this, if the set temperature to be changed is lower than the present set temperature (decrease of the set temperature), the temperature changing feed back illumination pattern may be a pattern of which a color temperature of the lighting makes a transition toward a low temperature.

For example, if the present set temperature is 18 degrees, the present set temperature is lighted with a blue color light, if 26 degrees, lighted with a green color light, and 30 degrees, lighted with an orange or yellow light. If a change of the set temperature is requested (request to change the temperature to 19 degrees) with the input in a state in which the lighting unit 70 is lighted in a basic color (for example, white), in FIG. 12A(A), which indicates that the air conditioning is at the present set temperature of 18 degrees, the lighting is changed to a color in FIG. 12A(B) (a lighting having a color temperature between blue color and green color) matched to the present set temperature (for example, 18 degrees). The user can understand a level of the present set temperature from the color of the lighting, intuitively.

In the meantime, an amount of change of the set temperature (hereafter, a "set temperature change amount") may vary with a number of inputs of the set temperature change amount through the input. For example, the set temperature change amount may be proportional to a number of pressing down of a set temperature change amount button. The lighting color may be changed as a response to each of the set temperature change requests, and the color of the lighting may be changed step by step reflecting the set temperature change amount matched to the number of change requests.

Thereafter, the lighting may make transition toward a color in FIG. 12A(C) a lighting color having the color temperature closer to the green color) matched to a set temperature value (19 degrees) requested to change, and the lighting may be maintained for a preset or predetermined time period in this state in FIG. 12A(D). After the set time period has passed, the lighting may be changed to white in FIG. 12A(F), which is the basic color, again. In this process, the lighting color may be changed to white, not instantly, but through gradation in which the lighting color is between the color matched to the 19 degrees and the basic color in FIG. 12A(E).

FIGS. 12B(A)~12B(E) illustrate an embodiment of a feed back light pattern when a flow rate is changed as an example of information description lighting. The air conditioner may include an input to receive a setting on a flow rate or strength of wind from the user, and the air conditioning control module 210 may control the air conditioning unit 400 according to the flow rate thus set. If the flow rate is changed through the input, the control unit 200 may compose or display a feed back illumination pattern for the flow rate change. The feed back illumination pattern may be provided to notify the user of a regular input of a flow rate change request, and has an effect of enabling to perform the notifying function with the lighting without a separate display.

When the flow rate is changed through the input, the pattern connecting module 230 may connect or match the feed back illumination pattern of the illumination patterns stored in the storing unit 500 to a flow rate change matched thereto, and the lighting control module 220 may generate a control signal according to the feed back illumination pattern connected thus (hereafter, "flow rate change feed back illumination pattern"), and apply the control signal to the lighting drive unit 300. In this case, the flow rate change feed back illumination pattern may be composed to display brighter lighting as the flow rate increases. As described above, the luminance of the lighting may be controlled by the luminance composing module 320.

The flow rate change feed back illumination pattern may indicate an increase or decrease in the flow rate with a pattern for which luminance varies. If a flow rate to be changed is higher than the present flow rate (the flow rate increases), the pattern may transition toward brighter lighting, and opposite to this, if the flow rate to be changed is lower than the present flow rate (the flow rate decreases), the pattern may transition toward darker lighting.

In a state in which the lighting is the basic color (for example, white, in FIG. 12B(A)), which indicates that air conditioning is underway, if a flow rate change (for example, flow rate increase) is requested through the input, a luminance of the lighting may be matched to the present flow rate in FIG. 12B(B). The user may understand a level of the present flow rate from the luminance of the lighting, intuitively. Whenever the increase in the flow rate is input repeatedly thought the input, the luminance of the lighting may become brighter step by steps in FIG. 12B(C) and in FIG. 12B(D), and after the lighting with the luminance matched to the flow rate changed is maintained for a preset or predetermined time period, the lighting may return to the basic color, again in FIG. 12B(E).

FIGS. 12C(A1)~12C(B3) illustrate another embodiment of a feed back light pattern when a flow rate is changed as an example of information description lighting. The flow rate change feed back illumination pattern may be embodied or displayed with animated lighting in which a predetermined descriptor may change a position on the illumination plate 60. A moving speed of the descriptor may be set to vary with a set flow rate, wherein the higher the set flow rate, the faster the moving speed. By turning on an array of the light source elements 71 in succession and turning the array off in succession, starting from ones turned on first, a mode of the lighting may be embodied in which a descriptor P moves in a fixed direction of FIG. 12C(A1)→FIG. 12C(A2)→FIG. 12C(A3). The descriptor P may be certain turned on ones of the plurality of the light source elements 71 arranged to form a closed path circulating the closed path. In this case, a fore end P1 of the descriptor P heading in the moving direction may be the brightest, and a rear end P2 of the descriptor P may be the least bright, such that the brightness is graded in a section between the fore end P1 and the rear end P2, in which the brightness gradually decreases as the light source elements 71 go from the fore end P1 to the rear end P2.

FIGS. 12C(B1)~12C(B3) illustrate a mode in which a turned on descriptor P circles in a clockwise direction within a section (about ¼ of a circle). At a time of the flow rate change, though the descriptor P may circle a set or predetermined number of times for a preset or predetermined time period, a speed of circulation may vary with a level of the flow rate thus changed. In this case, if the flow rate change feed back illumination pattern is performed, that is, if the flow rate setting is changed in the middle of the circulation of the descriptor P, the circulation of the pattern performed presently will end, and a new flow rate change feed back illumination pattern having a circulation speed of the pattern changed according to the changed flow rate may be performed.

In a state in which the lighting is the basic color (for example, white, in FIG. 12C(B1)), which indicates that air conditioning is underway, if the flow rate change or a flow rate indication request (this may be a first request of a plurality of flow rate increase requests through the input) is received through the input, the descriptor P may be circulated at a speed matched to the present flow rate, in FIG. 12C(B2). The user can understand a level of the present flow rate from the circulation speed of the lighting, intuitively. Thereafter, if an increase in the flow rate is received from the input again, the circulation speed of the descriptor P may change, in FIG. 12C(B3). The circulation speed of the descriptor P may vary with increase/decrease of the flow rate thus requested.

FIGS. 12D(A)~12D(C) illustrate an embodiment of a feed back light pattern as an example of information description lighting. This embodiment suggests changing a color of some of the light source elements 71 in the illumination pattern as a response (feed back) to the user's input. Though this is suitable for notifying regular reception of a predetermined control order through the input, such as the remote controller, embodiments are not limited thereto.

For example, if the predetermined control order is received through the input in a state in which the lighting is a certain basic color (for example, a blue color), some of the light source elements 71 may be returned to an original basic color again after being changed to another color (for example, a white color), in FIG. 12D(B). Some of the light source elements 71 may be used as the descriptor P which notifies the feed back.

Figure 13:
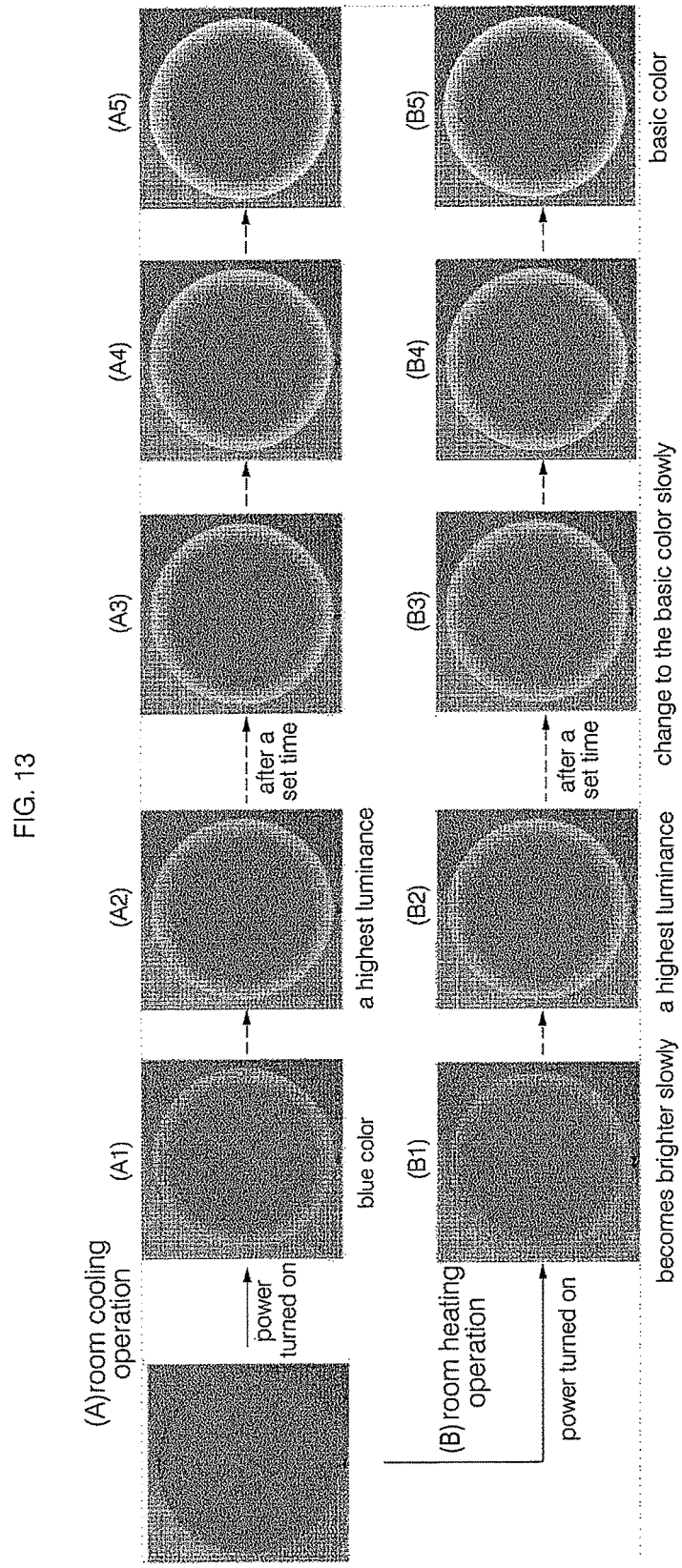
FIGS. 13(A1)~13(A5) illustrate a light pattern when a room cooling operation is performed as an example of information description lighting, and FIGS. 13(B1)~13(B5) illustrate a light pattern when a room heating operation is performed as an example of information description lighting.

FIGS. 13(A1)~13(A5) illustrate a light pattern when a room cooling operation is performed as an example of information description lighting. FIGS. 13(B1)~13(B5) illustrate a light pattern when a room heating operation is performed as an example of information description lighting.

The illumination pattern (hereafter, "cooling operation starting illumination pattern") when the room cooling operation is performed may be an illumination pattern in a case in which the room cooling operation is started from a state in which power is turned off. In order to allow a user to know by instinct that the operation is the room cooling operation upon seeing the color of the lighting, the cooling operation starting illumination pattern may include a step of turning on the light source elements 71 in a cold color group.

Referring to FIGS. 13(A1)~13(A4), upon reception of a room cooling operation request through an operator, such as the remote controller, in a state in which power is turned off, the light source elements 71 may be turned on in a blue color slowly, as shown in FIG. 13(A1), all of the light source elements 71 may be turned on at a fixed luminance, as shown in FIG. 13(A2), the lighting color may be changed to a basic color (for example, a white color) slowly after a predetermined time period has passed, as shown in FIG. 13(A3) and FIG. 13A4, and thereafter, white color lighting may be maintained during the room cooling operation, as shown in FIG. 13(A5).

A room heating operation starting illumination pattern may be an illumination pattern in a case in which the room heating operation is performed in a state in which power is turned off. In order to allow a user to know by instinct that the operation is the room heating operation upon seeing the color of the lighting, the heating operation starting illumination pattern may include a step of turning on the light source elements 71 in a warm color group.

Referring to FIGS. 13(B1)~13(B5), upon receipt of a room heating operation request through an operator, such as the remote controller, in a state in which power is turned off, the light source elements 71 may be turned on in an orange color slowly, as shown in FIG. 13(B1), all of the light source elements 71 may be turned on at a fixed luminance, as shown in FIG. 13(B2), the lighting color may be changed to a basic color (for example, the white color) slowly after a predetermined time period has passed, as shown in FIG. 13(B3) and FIG. 13(B4), and thereafter, white color lighting may be maintained during the room heating operation, as shown in FIG. 13(B5).

Figure 14:
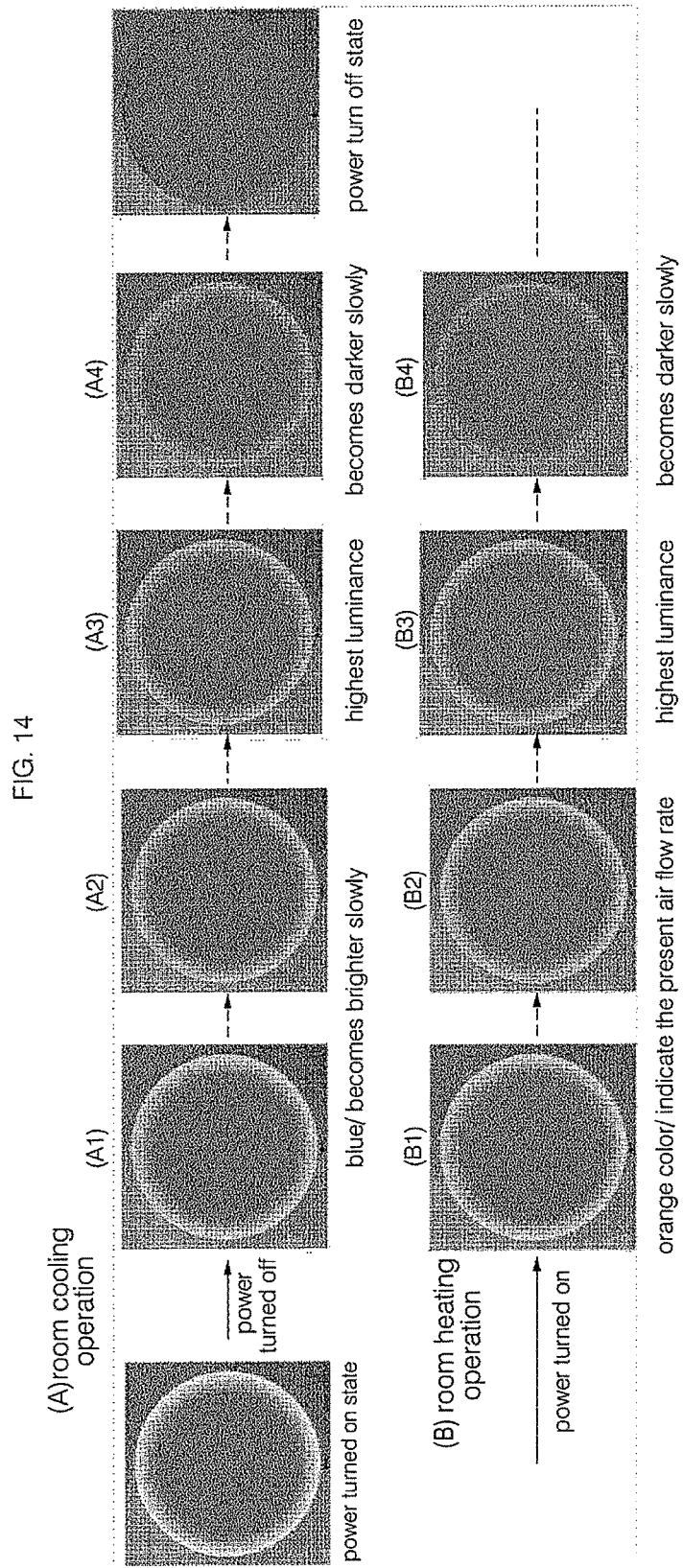
FIGS. 14(A1)~14(A4) illustrate a light pattern when power is turned off in a state in which a room cooling operation is set as an example of information description lighting, and FIGS. 14(B1)~14(B4) illustrate a light pattern when power is turned off in a state in which a room heating operation is set as an example of information description lighting.

FIGS. 14(A1)~14(A4) illustrate a light pattern when power is turned off in a state in which a room cooling operation is set as an example of information description lighting. FIGS. 14(B1)~14(B4) illustrate a light pattern when power is turned off in a state in which a room heating operation is set as an example of information description lighting.

The air conditioner may be lighted in the basic color (hereafter, for example, the white color) during which an air conditioning operation of the room cooling operation or the room heating operation is underway (power is turned on). The air conditioner according to embodiments suggests a change in the lighting made different depending on kinds of air conditioning operations performed at a time point of a power turn off request.

Referring to FIGS. 14(A1)~14(A4), when power turn off is requested in the middle of the room cooling operation through the operator, such as the remote controller, the light source elements 71 may be turned on in the cold color (hereinafter, for example, a blue color) slowly, as shown in FIG. 14(A1) and FIG. 14(A2), blue color lighting of a fixed luminance may be maintained for a preset or predetermined time period, as shown in FIG. 14(A3), the lighting may be darkened slowly, as shown in FIG. 14(A4), and the lighting may be turned off (a power turn off state). Upon reception of the power turn off request, not all of the lighting may be turned off at a same time, to enable the user to be notified that it has been a room cooling operation with the cold color group lighting.

Referring to FIGS. 14(B1)~14(B4), if power turn off is requested in the middle of the room heating operation through the operator, such as the remote controller, the light source elements 71 may be turned on in the warm color group (hereafter, for example, an orange color) slowly, as shown in FIG. 14(B1) and FIG. 14(B2), orange color lighting of a fixed luminance may be maintained for a preset or predetermined time period, as shown in FIG. 14(B3), the lighting may be darkened slowly, as shown in FIG. 14(B4), and the lighting may be turned off (a power turned off state). Upon reception of the power turn off request, not all of the lighting may be turned off at a same time, to enable the user to notify that it has been a room heating operation with the warm color group lighting.

Figure 15:
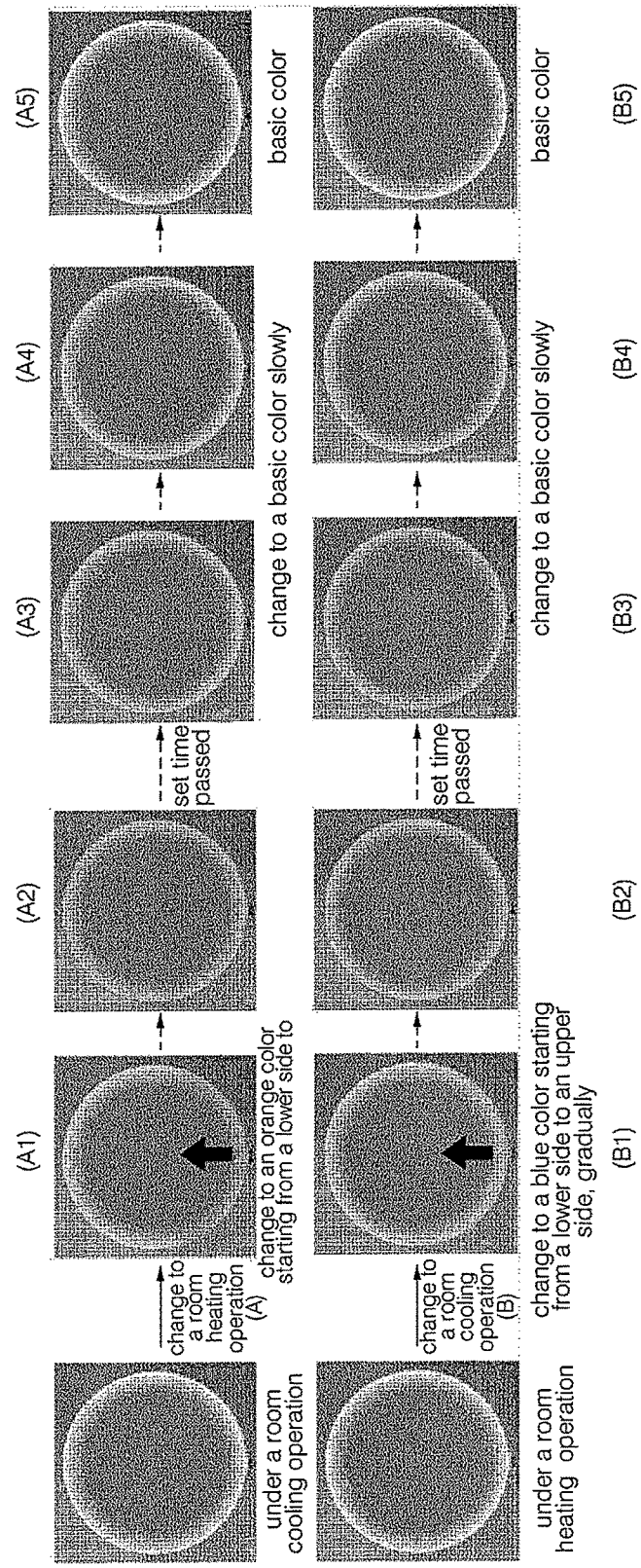
FIGS. 15(A1)~15(A5) illustrate a light pattern when a room cooling operation is changed to a room heating operation, and FIGS. 15(B1)~15(B5) illustrate a light pattern when a room heating operation is changed to a room cooling operation.

FIGS. 15(A1)~15(A5) illustrate a light pattern when a room cooling operation is changed to a room heating operation. FIGS. 15(B1)~15(B5) illustrate a light pattern when a room heating operation is changed to a room cooling operation.

Referring to FIGS. 15(A1)~15(A5), upon receipt of the room heating operation request in the middle of the room cooling operation (a lighting color at this time may be a basic color, for example, a white color) through the operator, such as the remote controller, the light source elements 71 may be turned on in the warm color group (hereafter, using an orange color, for example) slowly, as shown in FIG. 15A1. In this case, all of the light source elements 71 in a state of being turned on in the white color do not change to the orange color at a same time, but rather, a plurality of the light source elements 71 arranged to form the predetermined closed path may be gradually changed to the orange color slowly starting from ones arranged on a lower side thereof to ones arranged on an upper side thereof in succession, as shown in FIG. 15(A2). Accordingly, an annular bright portion formed on the illumination plate 60 may be changed gradually starting from a lower side to an upper side thereof.

When a preset or predetermined time period has passed in a state in which all of the light source elements 71 are turned on in the orange color, as shown in FIG. 15(A3), the color of all of the light source elements 71 may become lighter gradually, as shown in FIG. 15(A3) and FIG. 15(A4), until the color changes to a white color, which is the basic color, in FIG. 15(A5).

Referring to FIGS. 15(B1)~15(B5), if the room cooling operation is requested in the middle of the room heating operation which is lighted in the white color, the basic color, through the operator, such as the remote controller, the light source elements 71 may be turned on in the cold color group (hereafter, for example, a blue color) slowly, as shown in FIG. 15(B1). In this case, all of the light source elements 71 in a state of being turned on in the white color may not be changed to the blue color at a same time, but rather, a plurality of the light source elements 71 arranged to form the predetermined closed path may be gradually changed to the blue color slowly starting from ones arranged on a lower side thereof to ones arranged on an upper side thereof in succession, as shown in FIG. 15(B2). Accordingly, an annular bright portion formed on the illumination plate 60 may be gradually changed starting from the lower side to the upper side thereof.

When a preset or predetermined time period has passed in a state of FIG. 15(B3) where all of the light source elements 71 are turned on in the blue color, the color of all of the light source elements 71 may become lighter gradually, as shown in FIG. 15(B3) and FIG. 15(B4), until the color becomes the white color, which is the basic color, as shown in FIG. 15(B5).

In the meantime, the therapy lighting may be selected with the function selection module 110. Input of the setting on the therapy lighting thus selected may be made through the setting input module 120. In the setting on the therapy lighting, there may be a color, a luminance, scheduling of turn on, and a turn on time of the lighting of the illumination pattern, for example. Though input of the setting may be done by the user, if there is no separate setting, the setting may be made according to a setting made already and stored in the storing unit 50.

The pattern connecting module 230 may connect or match one of the therapy illumination patterns stored in the storing unit 500 to the therapy lighting selected with the function selection module 110. If there is a setting input through the setting input module 120, the pattern connecting module 230 may connect or match a therapy illumination pattern taking the additional setting into account. In this case, the pattern connecting module 230 may change the therapy illumination pattern existing in the storing unit 500. For example, if colors of a pattern are received from the setting input module 120, colors of an existing therapy illumination pattern may be revised. The lighting control module 220 may generate a control signal according to the illumination pattern thus connected, and apply the control signal to the lighting drive unit 300.

There are color therapies for healing a human body using lights of different frequencies. These are therapies in which waves or particles of colors resonate with a brain wave to stimulate the brain to boost vitality of the human body, and provide a calming effect, enabling balance between mind and body. Characteristics and Healing Effects of colors are as shown in Table 1 below.

TABLE 1

| COLOR | FUNCTION | HEALABLE DISEASE | CONTRADICTORY DISEASE |
|---|---|---|---|
| Red | Symbol of life, power, and vitality<br>Accelerates blood circulation, stimulates sympathetic nerve, invigorates liver and muscle tissue, and accelerates growth of plant<br>Effective for healing general decline of functions with a strong healing effect.<br>A wake-up effect | Healing of anemia, asthma, bronchitis, blood ionization symptom, endocrine system disorders, lethargy, stroke, pneumonia, tuberculosis, and paralysis | Emotional disturbance, such as anxiety, emotional disorder, mental illness, hypertension, neuritis, high fever, and inflammation |
| Orange | Symbol of feminine energy, and creative energy<br>Gives an influence both to physical vitality and intelligence and has a function of balance<br>Symbol of pleasure and happiness<br>Stimulant, raises blood pressure, and boosts power emotionally | Depressive disorder, muscle cramp, and paralysis | |
| Yellow | Symbol of mind and intelligence<br>Invigorates a motor system, and generates muscle energy<br>Mental stimulant<br>As a mental stimulant, as a first effect, makes patient pleasant, and, later, induces the patient to a half asleep and half awake state to heal neurasthenia or tuberculosis. | Eases from imperative idea, thinking, sentiment, and habit, utilized for psychology counseling effectively<br>Invigorates motor system, and muscle energy, and heals rheumatism, arthritis, eczema, skin diabetes, dyspepsia, liver disease, dehydration, depressive disorder, and stroke<br>Malasseziifurfur cell growth inhibition | Acute inflammation, diarrhea, fever neuralgia, excitement, and palpation |
| Green | Has functions of balance and harmony<br>Aseptic attribution, detoxication function<br>Relaxes, and stabilizes mind and body, reduces blood pressure, hypnotic action, reduces coagulation of blood, forms muscle tissue and skin, strengthens declining organs<br>Has an action of reducing blood pressure, and influences nerves to act as a stabilizer, or a somnifacient to heal overdelicate, neuralgia, headache, fret, neurotic anxiety, and shell shock.<br>Induces pleasant sensibility<br>Induces relaxation sensibility | Cellular tissue destruction effect, tumor healing, laryngitis, malaria, mental illness, insomnia, ulcer, overdelicate, extreme fatigue, neuralgia, headache, fret, and neurotic anxiety, | |
| Blue | Symbol of peace and calmness, and has a function of meditation<br>Characteristics opposite to a red light, accelerates oxidation, inhibits hormone activity, and serves as antiseptic in tissue, contracts muscle and blood vessel, and makes balance and harmony for making blood to circulate regularly<br>Contracts artery, raises blood pressure, a tonic and antiseptic for blood, and effective for skin diseases, rheumatism, and different inflammations | Eases tension and excitement<br>Jaundice, insomnia, cataract, glaucoma, ocular inflammation, epilepsy, burns, bald head, hysteria, pruritus, laryngitis, menstrual irregularity, polio, tonsillitis, thyroid gland, and head ache | |
| Indigo | Frees mind from fear, suppression, and has a function for healing psychological dissatisfaction | Diseases connected to eyes and ears | |
| Magenta | Utilizes in view of emotion if turned to pink color, mostly | Heals tinnitus, benign cystic tumor, and peeled off retina | |

TABLE 1-continued

| COLOR | FUNCTION | HEALABLE DISEASE | CONTRADICTORY DISEASE |
|---|---|---|---|
| White | Makes people younger by making a face or appearance distinctive and invigorating poor secretion. Makes to have an urge to exercise by accelerating mental thoughts, and physical activities. Induces pleasant sensibility Induces relaxation sensibility | | |
| Black | A color giving negative and passive feelings, and almost do not use in psychotherapy. | | |

Figure 21:
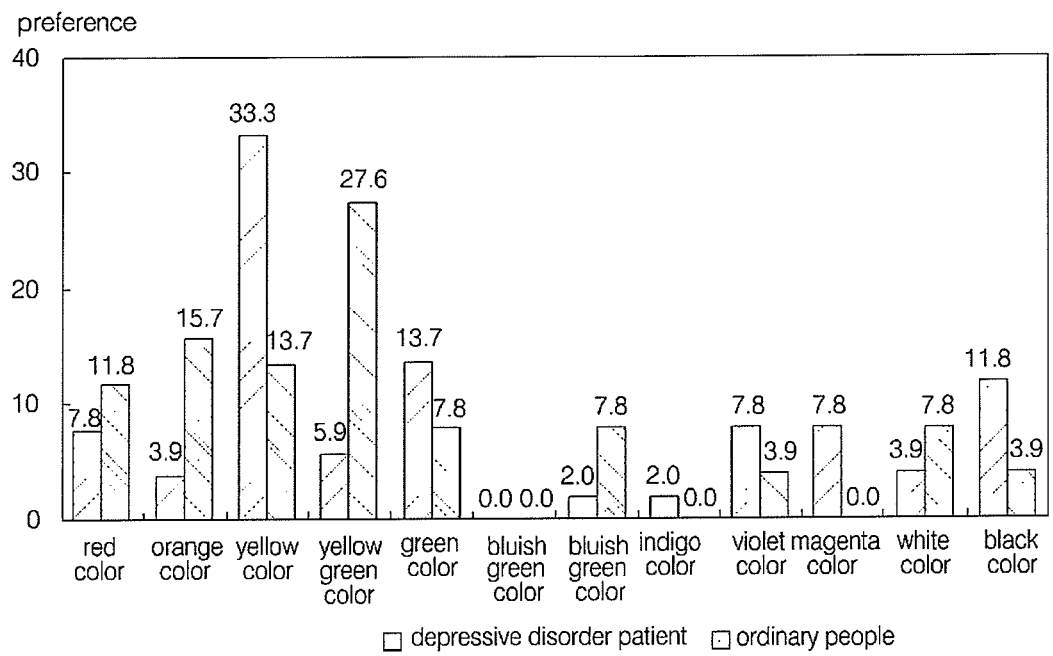
FIG. 21 is a graph showing comparison of preferences by ordinary persons and depressive disorder patients.

FIG. 21 is a graph showing comparison of preferences by ordinary persons and depressive disorder patients. Functions and effects of the therapy lighting will be described.

Figure 16A:
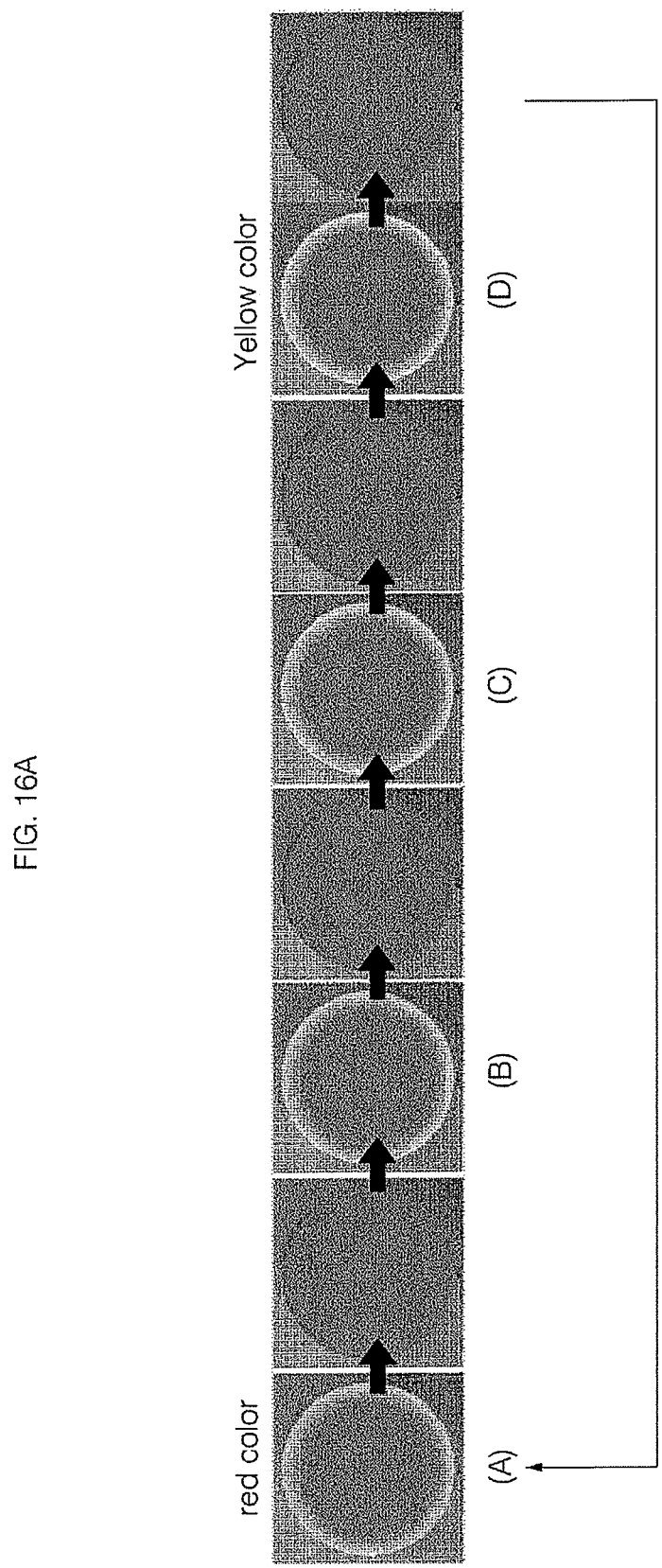
FIGS. 16A(A)~16A(D) illustrate a blood circulation acceleration lighting as an example of therapy lighting.

The therapy lightings will be described, with reference to FIGS. 16(A) to 16(D). FIGS. 16A(A)~16A(D) illustrate a pattern of blood circulation acceleration lighting as an example of the therapy lighting. The blood circulation acceleration lighting has a lighting-up pattern which is a combination of colors based on an orange color light, a yellow color light and/or color lights existing between regions of above colors in a visible light spectrum. The colors may be displayed in circulation.

Between lighting-up of the orange color in FIG. 16A(A) and the yellow color in FIG. 16A(D), the colors in FIG. 16A(B) and FIG. 16A(C) existing in a middle region of above colors in the visible light spectrum may be lighted-up. Each of the color lights may have a luminance that increases gradually in lighting-up, and decreases gradually in turning off for lighting-up a next color light.

The blood circulation acceleration lighting has effects of accelerating blood circulation in a human body, making a circulation system smooth, invigorating an endocrine system and a digestive system to improve natural healing capability, and enhancing active energy.

FIGS. 16B(A)~16B(C) illustrate a relaxation lighting as an example of therapy lighting. The relaxation lighting has a lighting-up pattern which is a combination of colors based on a green color light, a blue color light and/or colors existing between regions of above colors in a visible light spectrum. The colors may be displayed in circulation.

Between lighting-up of the green color light in FIG. 16B(A) and the blue color light in FIG. 16B(D), colors in FIG. 16B(B) existing in a middle region of above colors in the visible light spectrum may be turned on. Each of the color lights may have a luminance that increases gradually in lighting-up, and decreases gradually in turning off for lighting-up a next color light.

The relaxation lighting has colors which give hope and stability, ease tension enabling balance, and have a calming effect to be effective for concentration and insomnia. The relaxation lighting also gives a feeling of satisfaction, not only improving business ability, but also is suitable for taking a rest due to it being cozy colors.

Figure 16C:
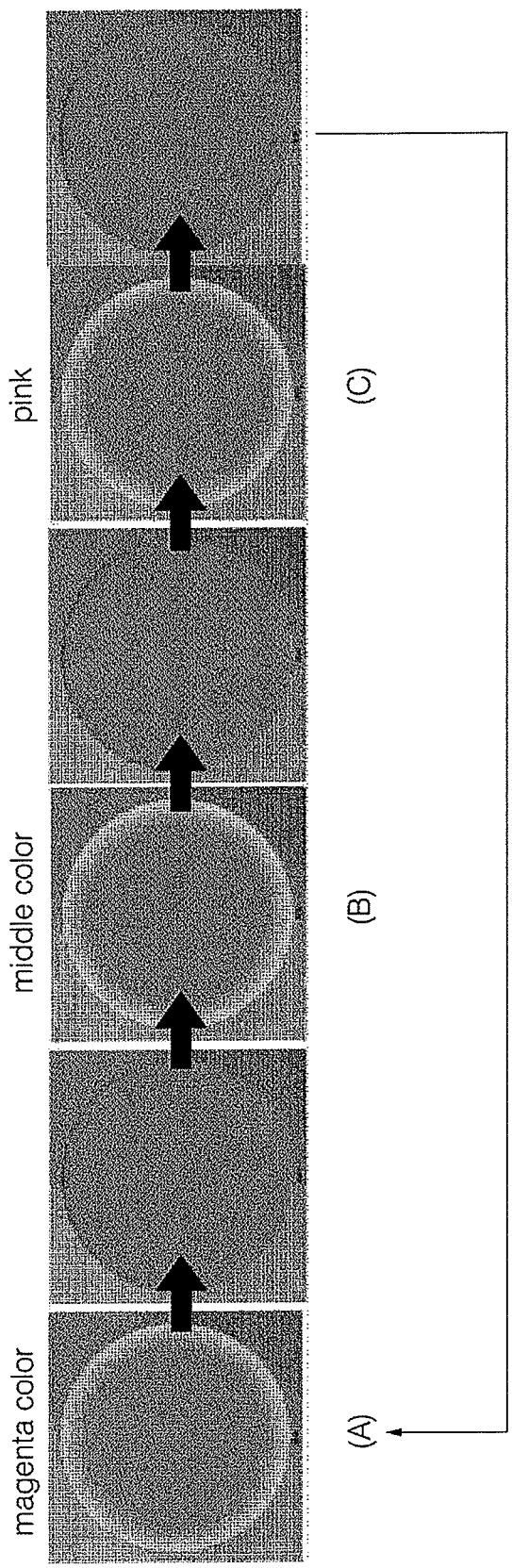
FIGS. 16C(A)~16C(C) illustrate a mediation lighting as an example of therapy lighting.

FIGS. 16C(A)~16C(C) illustrate a mediation lighting as an example of therapy lighting. The mediation lighting has a lighting-up pattern which is a combination of colors based on a violet color light, a pink color light and/or colors existing between regions of above colors in a visible light spectrum. The colors may be displayed in circulation.

Between lighting-up of the green color light in FIG. 16C(A) and the blue color light in FIG. 16C(C), colors in FIG. 16C(B) existing in a middle region of the above colors in the visible light spectrum may be turned on. Each of the color lights may have a luminance that increases gradually in lighting-up, and decreases gradually in turning off for lighting-up a next color light.

The meditation lighting gives purification and stability mentally, and acts on the parasympathetic nerve and pituitary gland. In particular, a violet color is good for moderation of pain, or healing of shock or morbid fear due to effects of giving an influence to a brain and a nervous system to calm down an oversensitive symptom. Further, it is well known that the pink color is a color of understanding and kindness representing maternal love. The pink color has an effect of calming down, suppressing secretion of norepinephrine which causes an aggressive action in the brain and body.

In the meantime, the mood lighting may be selected through the function selection module 110. A setting on the mood lighting thus selected may be input through the setting input module 120. As the setting on the mood lighting, there may be a color, a luminance, scheduling of a turn on time, and a turn on time period of the lighting of the illumination pattern. Though the setting may be input by the user, if there is no setting, the setting may be according to a setting made already and stored in the storing unit 500.

The pattern connecting module 230 may connect or match the mood lighting selected through the function selection module 110 to one of the mood illumination patterns stored in the storing unit 500. If there is an additional input through the setting input module 120, the pattern connecting module 230 may connect the mood lighting to one of the mood illumination patterns taking the additional input into account. In this case, the pattern connecting module 230 may also change the mood illumination pattern existing in the storing unit 500. For example, if colors of the illumination pattern are input through the setting input module 120 of the setting unit 100, the colors of the mood illumination pattern existing presently may be revised. The lighting control module 220 of the control unit 200 may generate a control signal according to the illumination pattern thus connected, and apply the control signal to the lighting drive unit 300.

FIGS. 17(A)~17(C) illustrate a mood lighting using a white light, and mood lighting using a yellow light, wherein the mood lightings have the same patterns with only a difference in color. The mood lighting may have a pattern in which a light of a designated color varies in luminance thereof, in an order of variation from bright to dark (in an order of FIGS. 17(A), 17(B), and 17(C)), or a reverse order of the above order (in an order of FIGS. 17(C), 17(B), and 17(A)). And, the pattern may be performed repeatedly (in an order of FIGS. 17(A), 17(B), 17(C), and 17(A)). Different from this, a circulating pattern in which repetition of an order of variation from dark to bright (in an order of FIGS. 17(A), 17(B), 17(C), 17(B), and 17(A)) may also possible.

The luminance of the light source elements 71 in the mood lighting may be controlled step by step or continuously by the luminance composing module 320.

FIG. 18 illustrates a perspective view of designation of a light color on a mobile terminal. Referring to FIG. 9, as described before, the air conditioner may include a wireless communication module 700 for communication with the mobile terminal 600. In this case, the color of the illumination pattern may be designated or set by the mobile terminal 600.

Referring to FIG. 18, upon running predetermined application software, an RGB color table 630 may be displayed on a screen of the mobile terminal, with which the user may designate the color at will. The user may designate the colors of the illumination pattern with the RGB color table 630 at will, and adjustment of detailed attributes, such as luminance, and so on, of the colors thus designated may also be possible. Depending on embodiments, it is possible to update the illumination patterns stored in the storing unit 500 according to the designated colors with the mobile terminal 600. If the mobile terminal 600 provides the function selection module 110 and/or the setting input module 120, the illumination pattern for which color is intended to be adjusted may be selected with the function selection module 110, detailed attributes, such as the color and the luminance of the illumination pattern thus selected, may be input with the setting input module 120, and the pattern connecting module 230 may connect the lighting intended to be displayed based on the input values with the illumination pattern stored in, or updated to, the storing unit 500.

FIGS. 19(A) to 19(E) illustrate examples of obzees displayed with lighting. FIGS. 20(A) to 20(F) illustrate patterns of obzees displayed with lightings.

Figure 19:
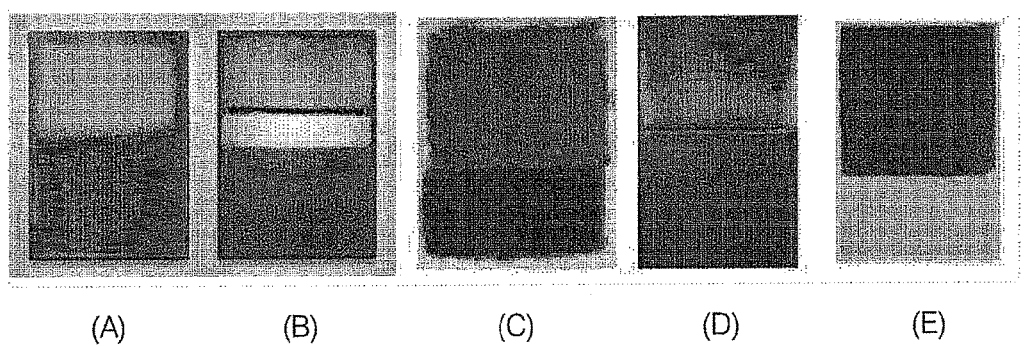
FIGS. 19(A) to 19(E) illustrate examples of obzees displayed with lighting, respectively.

Though FIGS. 19(A) to 19(E) illustrate rectangular abstract art paintings, the obzees displayable with the lighting are not limited to this, but a variety of obzees may be described depending on arrays of the lighting source elements 71. The obzee to be displayed may be selected with the function selection module 110. Depending on embodiments, the obzee may be selected in the middle of an air conditioning operation, as shown in FIG. 19(A). In this case, the lighting indicating that the air conditioning operation is underway becomes darker slowly, as shown in FIG. 19B, until the lighting is turned to the color of the obzee, as shown in FIG. 19(C).

A setting on the obzee thus selected may be input with the setting input module 120. The obzee intended to be displayed may be selected with the setting input module 120. If there is no separate setting input with the setting input module 120, the setting will be according to a setting previously set and stored in the storing unit 500.

The pattern connecting module 230 may connect or match the obzee selected with the function selection module 110 to one of the obzee illumination patterns stored in the storing unit 500. If there is an additional input through the setting input module 120, the pattern connecting module 230 may connect the obzee to one of the obzee illumination patterns taking the additional input into account. In this case, the pattern connecting module 230 may also change the obzee illumination pattern existing in the storing unit 500. For example, if the obzee intended to be displayed input with the setting input module 120 is changed, the obzee illumination pattern stored in the storing unit 500 may be changed.

The obzee may be embodied with a pattern based on colors of the obzee intended to displayed. FIGS. 20(A) to 20(F) illustrate an example of such illumination patterns for describing an obzee based on an orange color 1, a pink color 2, a red color 3, and a green color 4, wherein, if the obzee is selected in a state in which the lighting unit 70 is lighted in the white color (the basic color), colors may be lighted in an order of the orange color, the pink color, the red color, and the green color.

Figure 20:
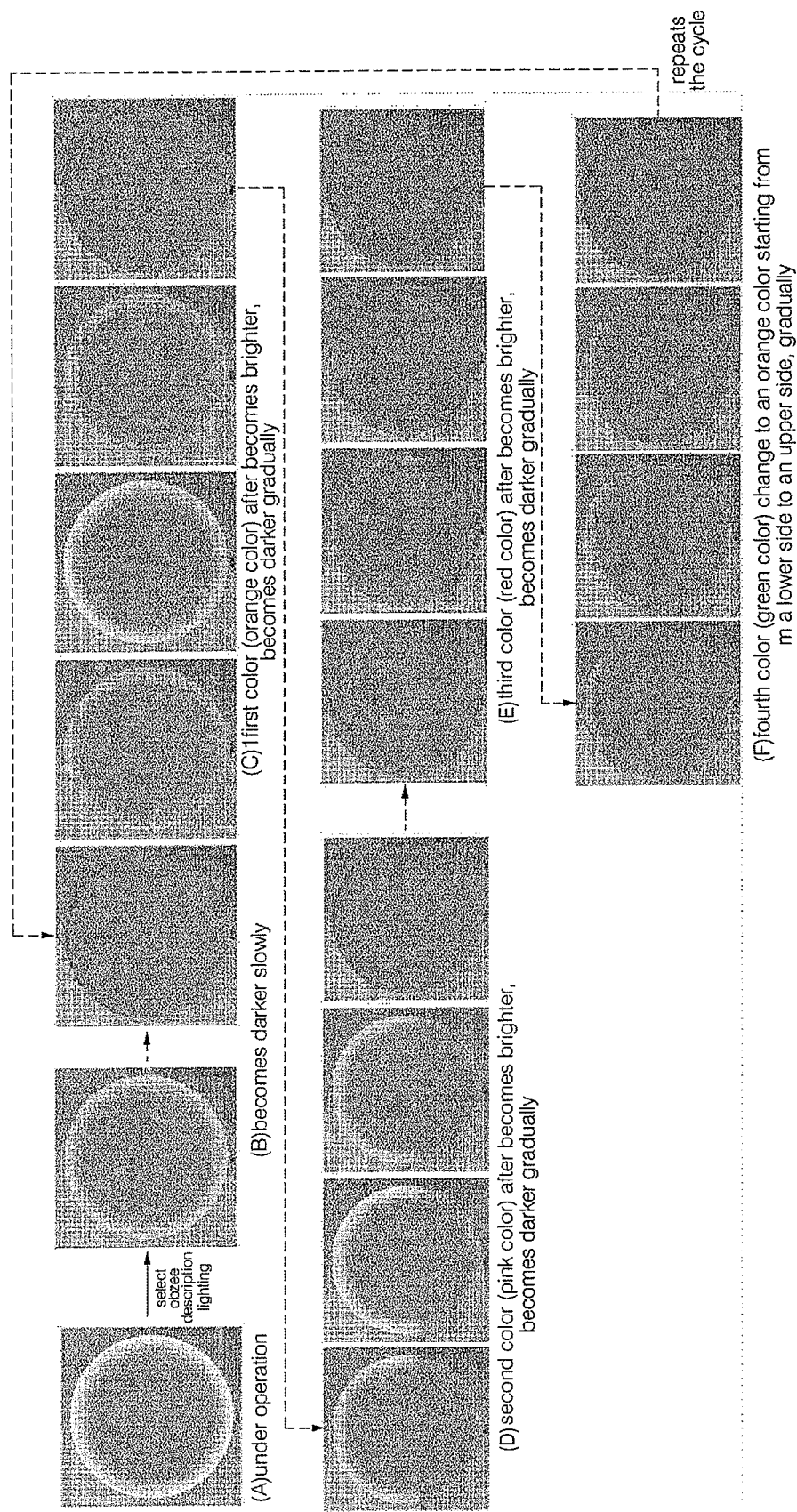
FIGS. 20(A) to 20(F) illustrate patterns of obzees displayed with lightings.

A change from one color to another color may be performed by, after a luminance of one color is darkened slowly, as shown in FIG. 20(B), the luminance of the other color may become bright until the luminance gradually becomes a predetermined level. The lighting having reached the predetermined luminance may be changed to a next lighting while slowly darkening again.

It is not required to turn on all of the light source elements 71 in the same color at one time, but two or more colors may be displayed. In this case, after some of the light source elements 71 are changed to the next color, first, colors surrounding the changed light source elements 71 may be changed in succession making an area displaying the changed color gradually larger while reducing an area of the color unchanged gradually (see FIGS. 20(A), 20(E), and 20(F)).

Figure 22:
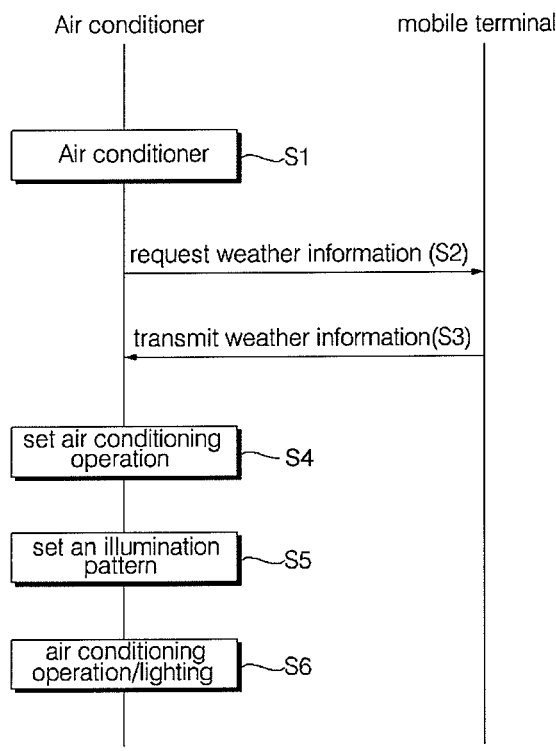
FIG. 22 is a flow chart of a method for controlling an air conditioner in accordance with an embodiment.

FIG. 22 is a flow chart of a method for controlling an air conditioner in accordance with an embodiment. Referring to FIGS. 9 and 22, the air conditioner may include a wireless compunction module 700 for communication with a mobile terminal 600. The control method to be described hereafter may be implemented in an air conditioner having the wireless communication module 700.

In a state of turning on, in step S1, the air conditioner may request information from the mobile terminal 600 (hereafter, "weather information") on a weather state, such as a room temperature of the region, season and time, weather, sunrise/sunset times, an outdoor temperature, and so on, with the wireless communication module 700, in step S2.

The mobile terminal 600 may access a distant information provider through an AP (Access Point) connected to a network, such as the Internet, to obtain the weather information, and the weather information thus obtained may be transmitted to the wireless communication module 700, in step S3.

At the time the turn on is scheduled, the air conditioner may set an illumination pattern based on the weather information received through the wireless communication module 700, in step S5, or perform an air conditioning operation, step S6, and more particularly, may drive a lighting unit 70 according to an illumination pattern thus set during the air conditioning operation.

The method for controlling an air conditioner thus described may be applied when the active lighting previously described is embodied or displayed, enabling not only to provide a more comfortable air conditioned environment according to a weather state, reflecting a turn on scheduled time, but also a user in a room to predict the weather state with the lighting.

Embodiments disclosed herein has been made in an effort to solve aforementioned problems, and embodiments disclosed herein provide an air conditioner which can embody or display different functions with lighting.

Embodiments disclosed herein further provide an air conditioner in which a lighting pattern may be connected or matched to a selected function and which may be lighted according to the lighting pattern thus connected.

Embodiments disclosed herein provide an air conditioner that may include a setting unit or device to set a predetermined function to be embodied or displayed with lighting, a storing unit or storage to store at least one illumination pattern information, a control unit or controller to connect the function input with the setting unit to an illumination pattern stored in the storing unit, and a lighting unit or apparatus to be lighted or lit according to the illumination pattern information connected by the control unit.

Embodiments disclosed herein further provide an air conditioner that may include a lighting unit or apparatus to be lighted or lit according to a predetermined illumination pattern, a setting unit or device to set a predetermined function to be embodied or displayed with lighting, a storing unit or storage to store illumination pattern information on the function thus set with the setting unit, a control unit or controller to connect the function input with the setting unit to the illumination pattern information stored in the storing unit, and a lighting drive unit or drive to drive the lighting unit according to the illumination pattern information thus connected. The illumination pattern of the lighting unit may be matched to the illumination pattern information on the function set with the setting unit.

Embodiments disclosed herein further provide an air conditioner that may include a setting unit or device to set predetermined function to be embodied or displayed with lighting, a lighting unit or apparatus to embody or display the function thus set with the setting unit with a predetermined illumination pattern, a storing unit or storage to store information on illumination patterns classified according to functions to be embodied or displayed with the lighting, a pattern connecting module to connect or match the function set with the setting unit to information on an illumination pattern matched to the function, a lighting control module to output a control signal according to the information on the illumination pattern thus connected with the pattern connecting module, and a lighting drive unit or drive to drive the lighting unit in response to the control signal.

The air conditioner according to embodiments has an effect of notifying a user of a present situation of the present function with lighting without a separate display by connecting a selected function to the illumination pattern and describing the selected function with the lighting according to the illumination pattern. By embodying, not only room lighting, but also active lighting, information description lighting, mood lighting, or obzee description lighting, utilization of the lighting may be expanded.

It will be apparent that persons skilled in this field of art may carry out the present invention in other modes without changing technical aspects or essential characteristics of the present invention. Therefore, it is required to understand that the embodiments described herein are illustrative, but not limits the present invention in all aspects. Scope of the present invention is recited in following claims rather than the detailed description of the present invention, and it is required to interpret that all variations and modes of the variations derived from meanings and scopes of the claims, and concepts equivalent thereto.

Any reference in this specification to "one embodiment," "an embodiment," "example embodiment," etc., means that a particular feature, structure, or characteristic described in connection with the embodiment is included in at least one embodiment of the invention. The appearances of such phrases in various places in the specification are not necessarily all referring to the same embodiment. Further, when a particular feature, structure, or characteristic is described in connection with any embodiment, it is submitted that it is within the purview of one skilled in the art to effect such feature, structure, or characteristic in connection with other ones of the embodiments.

Although embodiments have been described with reference to a number of illustrative embodiments thereof, it should be understood that numerous other modifications and embodiments can be devised by those skilled in the art that will fall within the spirit and scope of the principles of this disclosure. More particularly, various variations and modifications are possible in the component parts and/or arrangements of the subject combination arrangement within the scope of the disclosure, the drawings and the appended claims. In addition to variations and modifications in the component parts and/or arrangements, alternative uses will also be apparent to those skilled in the art.

What is claimed is:

1. An air conditioner, comprising:
   a setting device to set a predetermined function to be embodied with lighting;
   a storage to store at least one illumination pattern information;
   a controller that connects the function input by the setting device to the at least one illumination pattern information stored in the storage; and
   a lighting apparatus having a plurality of color lights lit according to the at least one illumination pattern information by the controller, wherein the setting device includes:
      a function selection module to select the predetermined function to be embodied with lighting; and
      a setting input module to receive a setting on the function selected with the function selection module, wherein the at least one illumination pattern information includes information on a therapy illumination pattern formed based on an influence of a color on a human body, wherein the therapy illumination pattern has a circulation of colors between predetermined first and second colors in a visible light spectrum, and wherein each of the plurality of color lights lit by the lighting apparatus according to the therapy illumination pattern has a luminance that increases gradually during a lighting-up process and decreases gradually during a turning off process in order to light up a next color light.

2. The air conditioner of claim 1, wherein the setting input module includes a communication module in communication with an external information providing apparatus through a wire or wireless communication network to receive a setting on the function thus selected.

3. The air conditioner of claim 2, wherein the communication module receives update information to update the at least one illumination pattern information stored in the storage.

4. The air conditioner of claim 3, wherein the controller includes a pattern managing module to update the at least one illumination pattern information stored in the storage based on the update information.

5. The air conditioner of claim 1, wherein the at least one illumination pattern information comprises a plurality of illumination pattern information, and wherein the controller includes:
   a pattern connecting module to connect the function selected with the function selection module to one of the plurality of illumination pattern information matched thereto; and
   a lighting control module to generate a control signal to drive the lighting apparatus according to the one of the plurality of illumination pattern information connected with the function by the pattern connecting module.

6. The air conditioner of claim 5, further comprising a lighting drive to drive the lighting apparatus in response to the control signal.

7. The air conditioner of claim 6, wherein the control signal includes information on a color and information on a luminance of the lighting to be displayed by the lighting apparatus, and wherein the lighting drive apparatus includes:
- a color composing module to compose the color of the lighting to be displayed by the lighting apparatus according to information on the color; and
- a luminance composing module to compose the luminance of the lighting to be displayed by the lighting apparatus according to information on the luminance.

8. The air conditioner of claim 1, further comprising a wireless communication module to receive weather state information, wherein the controller connects the weather state information received from the wireless communication module to the at least one illumination pattern information stored in the storage.

9. The air conditioner of claim 1, wherein the at least one illumination pattern information further includes information on an active illumination pattern which reflects a surrounding environment at a time of turning on the air conditioner.

10. The air conditioner of claim 9, wherein the active illumination pattern includes a weather illumination pattern for which the lighting apparatus displays a descriptor of a warm color group, including yellow, orange, or red, when a predetermined scheduled condition is met.

11. The air conditioner of claim 10, wherein the active illumination pattern further includes a weather illumination pattern for which the lighting apparatus displays a descriptor of a cold color group, including blue or violet, when a predetermined scheduled condition is met.

12. The air conditioner of claim 9, further comprising a wireless communication module to receive information on a surrounding environment.

13. The air conditioner of claim 1, wherein the therapy illumination pattern includes a blood circulation acceleration illumination pattern which has a circulation of an orange color as the first color and a yellow color as the second color.

14. The air conditioner of claim 1, wherein the therapy illumination pattern includes a relaxation illumination pattern which has a circulation of a green color as the first color and a blue color as the second color.

15. The air conditioner of claim 1, wherein the at least one illumination pattern information further includes a mood illumination pattern for which the lighting apparatus varies the lighting according to a setting already made, and wherein the air conditioner further includes a wireless communication module in communication with an external information providing apparatus through a wireless communication network to receive information on a color of the mood illumination pattern.

16. The air conditioner of claim 1, wherein the at least one illumination pattern information further includes information on an information description illumination pattern displayed by the lighting apparatus as a response to a control order received from a predetermined remote controller.

17. The air conditioner of claim 1, wherein the at least one illumination pattern information further includes information on an image description illumination pattern for which the lighting apparatus displays an image which reminds a user of a predetermined description object.

18. The air conditioner of claim 1, wherein the lighting apparatus comprises a plurality of lighting source elements.

19. The air conditioner of claim 18, wherein the plurality of lighting source elements are arranged along an annular path.

20. The air conditioner of claim 19, wherein the plurality of lighting source elements are arranged along a closed annular path.

21. The air conditioner of claim 18, wherein each of the plurality of light source elements comprises a LED or LCD capable of emitting red light, green light, blue light, or a combination thereof.

22. The air conditioner of claim 18, wherein the lighting apparatus further comprises a frame and a illumination plate mounted in the frame.

23. The air conditioner of claim 22, wherein the illumination plate is convex with respect to the body.

24. The air conditioner of claim 18, further comprising:
- a heat exchanger;
- a fan assembly;
- an air inlet, through which the fan assembly draws air into the body to perform heat exchange with the heat exchanger;
- a plurality of outlets through which the heat exchanged air is discharged.

25. The air conditioner of claim 18, wherein the lighting apparatus covers an entire of the front surface of the body.

26. The air conditioner of claim 18, wherein a flow passage is formed between the lighting apparatus and the body.

27. The air conditioner of claim 26, wherein the lighting apparatus is movable in a first direction in which light shines perpendicular to a surface of the lighting apparatus and a second direction opposite to the first direction with respect to the body.

28. The air conditioner of claim 1, wherein the first predetermined color is orange and the second predetermined color is yellow, or the first predetermined color is green and the second predetermined color is blue.

29. The air conditioner of claim 24, wherein when the user increases a speed of the fan assembly, the plurality of lighting source elements are sequentially turned on and off.

30. An air conditioner, comprising:
- a lighting apparatus having a plurality of color lights to be lit according to a predetermined illumination pattern;
- a setting device to set a predetermined function to be embodied with lighting;
- a storage to store at least one illumination pattern information on the function thus set with the setting device;
- a controller to connect the function input with the setting device to the at least one illumination pattern information stored in the storage; and
- a lighting drive to drive the lighting apparatus according to the at least one illumination pattern information connected to the function, wherein the predetermined illumination pattern of the lighting apparatus is matched to the at least one illumination pattern information associated with the function set with the setting device, wherein the setting device includes:
  - a function selection module to select the predetermined function to be embodied with lighting; and
  - a setting input module to receive a setting on the function selected with the function selection module, wherein the at least one illumination pattern information includes information on a therapy illumination pattern formed based on an influence of a color on a human body, wherein the therapy illumination pattern has a circulation of colors between predetermined first and second colors in a visible light spectrum, and wherein each of the plurality of color lights lit by the lighting apparatus according to the therapy illumination pattern has a luminance that increases gradually during a lighting-up process and decreases gradually during a turning off process in order to light up a next color light.

31. The air conditioner of claim 30, wherein the at least one illumination pattern information further includes information on an active illumination pattern which reflects a surrounding environment at a time of turning on the air conditioner.

32. The air conditioner of claim 30, wherein the therapy illumination pattern includes a blood circulation acceleration illumination pattern which has a circulation of an orange color as the first color and a yellow color as the second color.

33. The air conditioner of claim 30, wherein the therapy illumination pattern includes a relaxation illumination pattern which has a circulation of a green color as the first color and a blue color as the second color.

34. The air conditioner of claim 30, wherein the at least one illumination pattern information further includes information on an image description illumination pattern for which the lighting apparatus displays an image which reminds a user of a predetermined description object.

35. The air conditioner of claim 30, wherein the lighting apparatus comprises a plurality of lighting source elements.

36. The air conditioner of claim 35, wherein the plurality of lighting source elements are arranged along an annular path, or a closed annular path.

37. The air conditioner of claim 35, wherein each of the plurality of light source elements comprises a LED or LCD capable of emitting red light, green light, blue light, or a combination thereof.

38. The air conditioner of claim 35, wherein the lighting apparatus covers an entire front surface of the body.

39. An air conditioner, comprising
a setting device to set a predetermined function to be displayed with lighting;
a lighting apparatus having a plurality of color lights to display the function thus set with a predetermined illumination pattern;
a storage to store information on a plurality of illumination patterns classified according to functions to be displayed with the lighting;
a pattern connecting module to connect the function set to information on an illumination pattern of the plurality of illumination patterns matched to the function;
a lighting control module to output a control signal according to the information on the illumination pattern connected to the function by the pattern connecting module; and
a lighting apparatus drive to drive the lighting apparatus in response to the control signal, wherein the setting device includes:
a function selection module to select the predetermined function to be embodied with lighting; and
a setting input module to receive a setting on the function selected with the function selection module, wherein the at least one illumination pattern information includes information on a therapy illumination pattern formed based on an influence of a color on a human body, wherein the therapy illumination pattern has a circulation of colors between predetermined first and second colors in a visible light spectrum, and wherein each of the plurality of color lights lit by the lighting apparatus according to the therapy illumination pattern has a luminance that increases gradually during a lighting-up process and decreases gradually during a turning off process in order to light up a next color light.

40. The air conditioner of claim 39, wherein the plurality of illumination patterns further includes an active illumination pattern which reflects a surrounding environment at a time of turning on the air conditioner.

41. The air conditioner of claim 39, wherein the therapy illumination pattern includes a blood circulation acceleration illumination pattern which has a circulation of an orange color as the first color and a yellow color as the second color.

42. The air conditioner of claim 39, wherein the plurality of illumination patterns further includes an image description illumination pattern for which the lighting apparatus displays an image which reminds a user of a predetermined description object.

43. The air conditioner of claim 39, wherein the lighting apparatus comprises a plurality of lighting source elements.

44. The air conditioner of claim 43, wherein the plurality of lighting source elements are arranged along an annular path, or a closed annular path.

45. The air conditioner of claim 43, wherein each of the plurality of light source elements comprises a LED or LCD capable of emitting red light, green light, blue light, or a combination thereof.

46. The air conditioner of claim 43, wherein the lighting apparatus covets an entire front surface of the body.

* * * * *